US010107806B2

(12) United States Patent
Martinell Gispert-Sauch et al.

(10) Patent No.: US 10,107,806 B2
(45) Date of Patent: Oct. 23, 2018

(54) APPARATUS FOR THE AUTOMATIC PERFORMANCE OF IMMUNOHAEMATOLOGY ANALYSIS ON GEL CARDS

(71) Applicant: GRIFOLS, S.A., Barcelona (ES)

(72) Inventors: Enrique Martinell Gispert-Sauch, Barcelona (ES); Jordi Puig Cebria, Barcelona (ES)

(73) Assignee: GRIFOLS, S.A., Barcelona (ES)

( * ) Notice: Subject to any disclaimer, the term of this patent is extended or adjusted under 35 U.S.C. 154(b) by 85 days.

(21) Appl. No.: 15/148,994

(22) Filed: May 6, 2016

(65) Prior Publication Data

US 2017/0023561 A1    Jan. 26, 2017

(30) Foreign Application Priority Data

Jun. 26, 2015  (ES) .................................. 201530927

(51) Int. Cl.
*G01N 33/543* (2006.01)
*G01N 35/10* (2006.01)
(Continued)

(52) U.S. Cl.
CPC .  *G01N 33/54366* (2013.01); *G01N 35/00029* (2013.01); *G01N 35/00722* (2013.01);
(Continued)

(58) Field of Classification Search
CPC .......... B01L 2200/141; B01L 2200/16; B01L 2300/0672; B01L 2300/0803;
(Continued)

(56) References Cited

U.S. PATENT DOCUMENTS 5,578,269 A    11/1996  Yaremko et al.
6,162,399 A  * 12/2000  Martinell Gisper-Sauch .............
                                         G01N 35/0099
                                              422/63
(Continued)

FOREIGN PATENT DOCUMENTS

EP           0629858 A1    12/1994
EP         0 895 087 A2     2/1999
(Continued)

OTHER PUBLICATIONS

Grifols erytra brochure, published Mar. 10, 2014 and useful as a 102a1/a2 reference.*

(Continued)

*Primary Examiner* — Benjamin R Whatley
(74) *Attorney, Agent, or Firm* — Knobbe, Martens, Olson & Bear, LLP

(57) ABSTRACT

The apparatus has a containing body with a flat upper functional floor for containing receptacles of reagents, diluents and samples, as well as housings for gel cards and incubators for the same; a lower floor containing receptacles for washing liquids and the collection of waste and cards and for housing the fluid control and electronic control system; a series of longitudinal and transverse guides associated with the upper part of the apparatus, suitable for carrying in suspension the moving heads of the apparatus, the heads being movable on the transverse guides; two heads, respectively for perforation and pipetting and for the transport of gel cards; two centrifuges and a gel card reader; and a folding touch screen providing information and control.

27 Claims, 31 Drawing Sheets

(51) Int. Cl.
  *G01N 35/04* (2006.01)
  *G01N 35/00* (2006.01)
  *G01N 35/02* (2006.01)
  *B01L 7/00* (2006.01)
  *B01L 9/06* (2006.01)

(52) U.S. Cl.
  CPC ..... *G01N 35/00732* (2013.01); *G01N 35/026* (2013.01); *G01N 35/04* (2013.01); *G01N 35/1009* (2013.01); *G01N 35/1079* (2013.01); *B01L 7/52* (2013.01); *B01L 9/06* (2013.01); *B01L 2200/141* (2013.01); *B01L 2200/16* (2013.01); *B01L 2300/0672* (2013.01); *B01L 2300/0803* (2013.01); *B01L 2300/0841* (2013.01); *B01L 2300/1822* (2013.01); *G01N 2035/009* (2013.01); *G01N 2035/0091* (2013.01); *G01N 2035/00148* (2013.01); *G01N 2035/00306* (2013.01); *G01N 2035/00356* (2013.01); *G01N 2035/00376* (2013.01); *G01N 2035/00495* (2013.01); *G01N 2035/00524* (2013.01); *G01N 2035/0477* (2013.01); *G01N 2035/1025* (2013.01); *G01N 2035/1048* (2013.01)

(58) Field of Classification Search
  CPC ..... B01L 2300/0841; B01L 2300/1822; B01L 7/52; B01L 9/06; G01N 2035/00306; G01N 2035/00356; G01N 2035/00376; G01N 2035/00495; G01N 2035/00524; G01N 2035/009; G01N 2035/0091; G01N 2035/0477; G01N 2035/1025; G01N 2035/1048; G01N 33/54366; G01N 35/00029; G01N 35/00722; G01N 35/00732; G01N 35/026; G01N 35/04; G01N 35/1009; G01N 35/1079
  See application file for complete search history.

(56) References Cited

U.S. PATENT DOCUMENTS

| | | | |
|---|---|---|---|
| 6,521,183 B1 | 2/2003 | Burri et al. | |
| 7,520,164 B1* | 4/2009 | Ayliffe | G01N 15/1056 324/71.1 |
| 2003/0089581 A1* | 5/2003 | Thompson | B65G 23/18 198/619 |
| 2006/0263250 A1* | 11/2006 | Blouin | B01L 3/021 422/63 |
| 2009/0223311 A1 | 9/2009 | Hamada et al. | |
| 2009/0293644 A1* | 12/2009 | Pellicer Sancho | G01N 35/025 73/863.01 |
| 2014/0106467 A1* | 4/2014 | Hutter | B01L 3/021 436/180 |
| 2014/0163920 A1 | 6/2014 | Jorgensen et al. | |
| 2014/0207526 A1* | 7/2014 | Noyes | G06Q 30/0283 705/7.35 |
| 2015/0111198 A1* | 4/2015 | Brisebat | G01N 35/0099 435/5 |
| 2016/0032358 A1* | 2/2016 | Buse | G01N 35/04 435/6.12 |

FOREIGN PATENT DOCUMENTS

| | | |
|---|---|---|
| EP | 0 895 087 A3 | 7/2000 |
| EP | 2 128 626 A2 | 12/2009 |
| EP | 2128626 A2 | 12/2009 |
| EP | 2 128 626 A3 | 11/2014 |
| JP | 11-108937 A | 4/1999 |
| JP | 2001-074750 A | 3/2001 |
| JP | 2002-286728 A | 10/2002 |
| JP | 2003-329692 A | 11/2003 |
| JP | 2006-329774 A | 12/2006 |
| JP | 2007-303885 A | 11/2007 |
| JP | 2009-288248 A | 12/2009 |
| JP | 2014-115291 A | 6/2014 |
| JP | 2014-532870 A | 12/2014 |
| WO | WO 2013-064665 A1 | 5/2013 |

OTHER PUBLICATIONS

Extended European Search Report dated Nov. 7, 2016 in European Application No. 16166497.4.

Office Action, dated Feb. 16, 2018, in Chilean Patent Application No. 2016-001268.

Office Action, dated Mar. 5, 2018, in Japanese Patent Application No. 2016-093689.

* cited by examiner

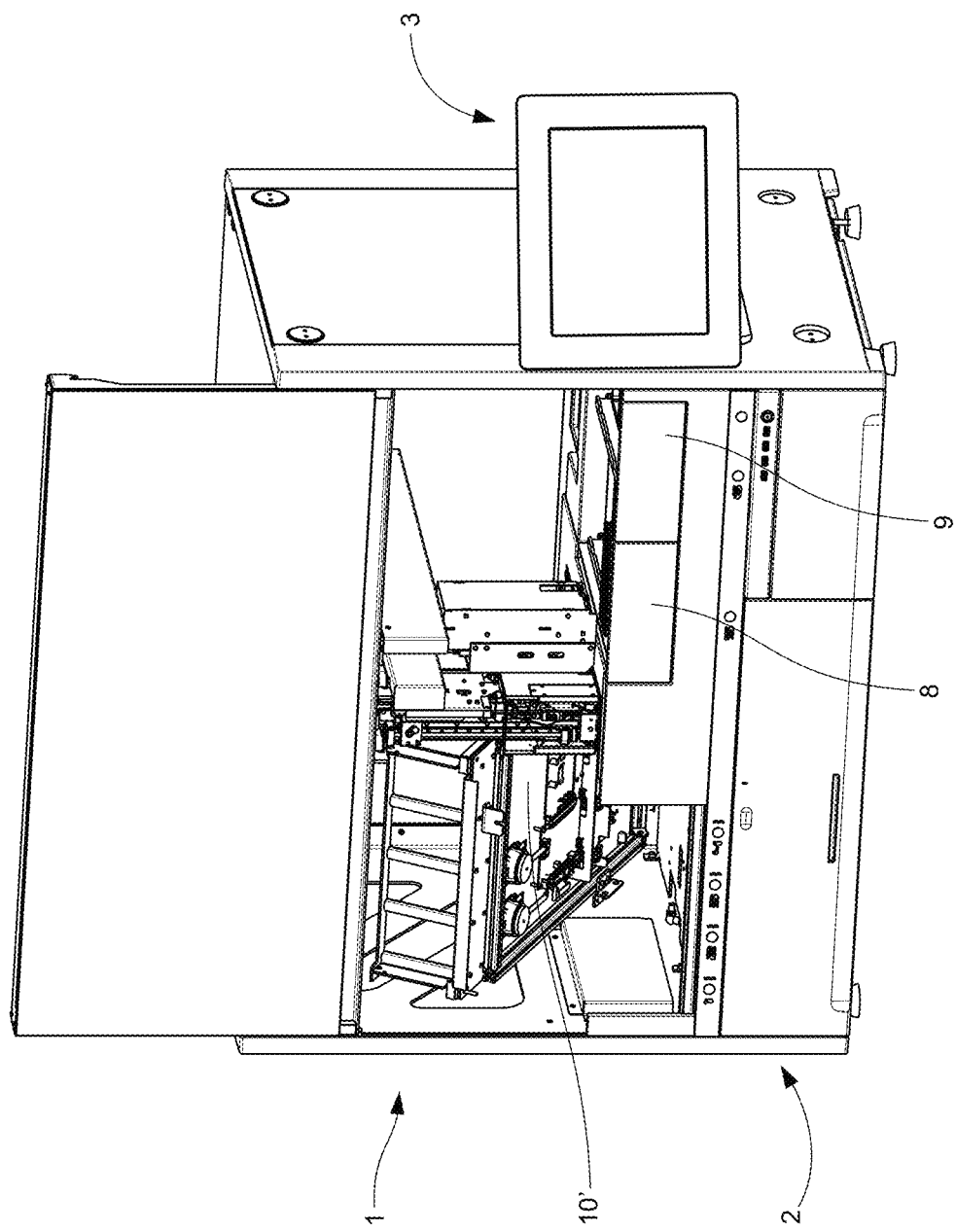
Fig. 1bis

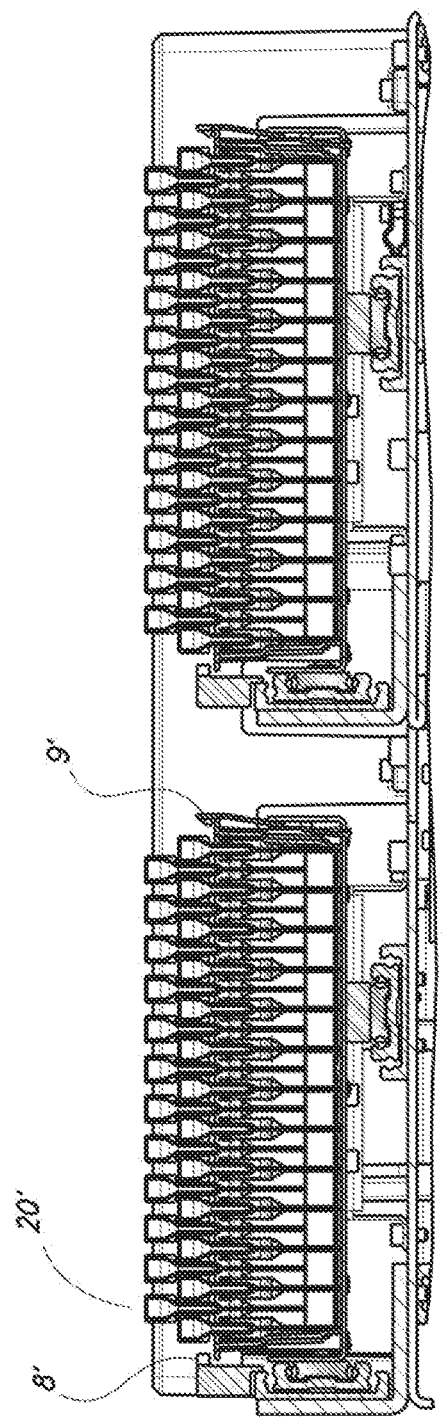

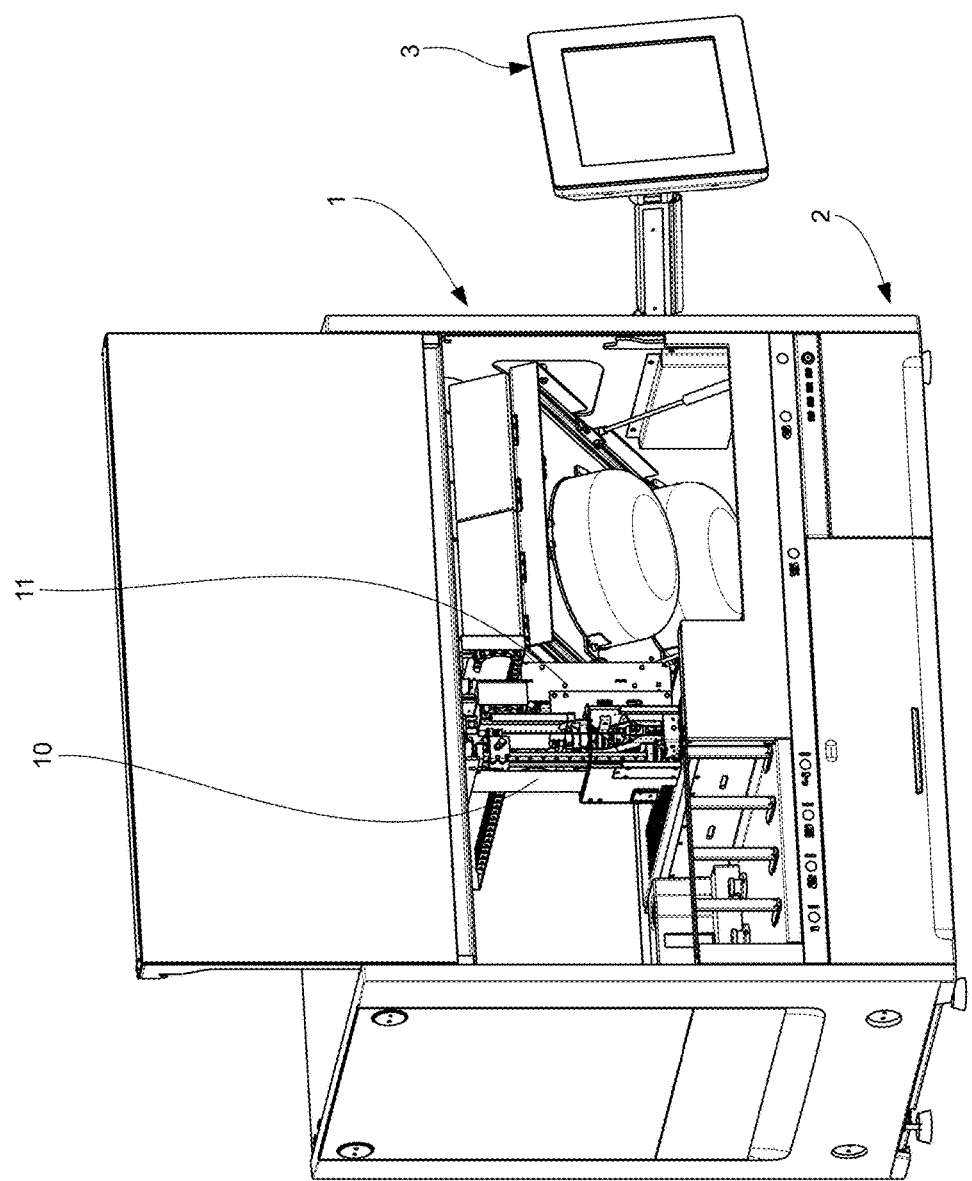
Fig. 5bis

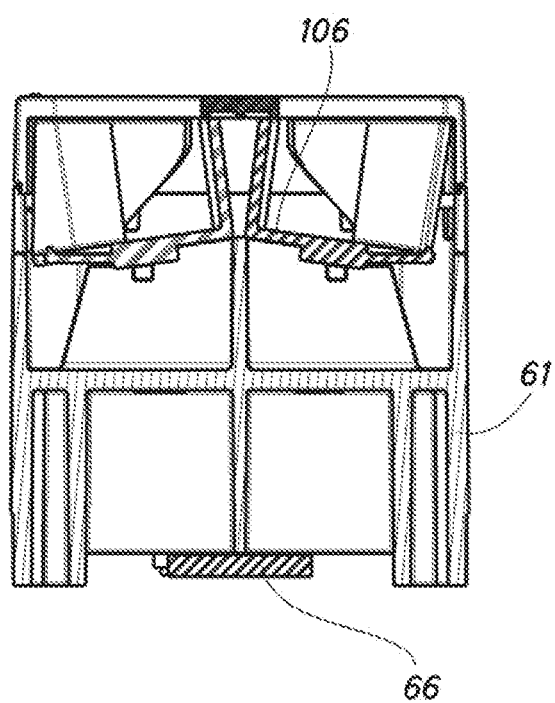
Fig. 14bis

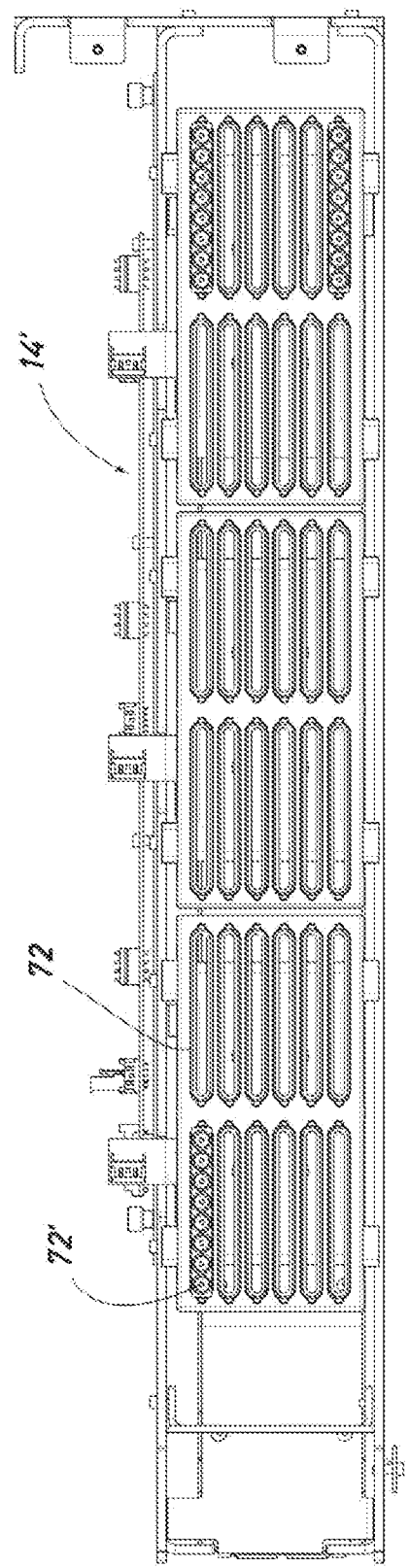
Fig. 18 bis

APPARATUS FOR THE AUTOMATIC PERFORMANCE OF IMMUNOHAEMATOLOGY ANALYSIS ON GEL CARDS

PRIORITY AND CROSS-REFERENCE TO RELATED APPLICATIONS

This application claims the benefit of the Spanish Patent Application No. P201530927 filed on Jun. 26, 2015, which is hereby incorporated by reference in its entirety.

FIELD

The present invention relates to the sector of immuno-haematological analysis, and in particular to an apparatus intended for the automatic analysis of blood samples on gel cards.

BACKGROUND

The purpose of this type of apparatus is the automatic analysis of blood samples in accordance with determined specifications.

However, experience in the use of this type of automated apparatus has shown that it would be desirable to have devices capable of automatically analysing blood samples at multiple locations and centres, and for this purpose it is essential to alter the architecture of the current devices in order to obtain certain different functional characteristics, smaller dimensions, ease of movement and economy, all with the full ability to carry out the entire process, i.e. from the moment of inserting the sample to the moment of obtaining the results of the test after the time required to carry out the entire analysis process.

SUMMARY

In some embodiments, to achieve its objectives, the apparatus forming the subject of the present invention is formed of a single enveloping body essentially of the "benchtop" type, i.e. intended to be attached to a work bench, so that all the elements of the apparatus are within ergonomic reach of the operator in a seated position, this being simply achieved by having an upper floor and a lower floor, between which the various elements and working areas are distributed in such a way that all samples, diluents, reagents and gel cards are handled in the upper floor, having means for receiving all of these elements as well as means for performing the dilutions of the samples and the pipetting of the different liquids, including the pipetting on the gel cards, which are stored in the same upper floor of the apparatus. In addition, the upper floor is also provided with identification and incubation means, as well as means of access to the means of centrifugation, reading, scrapping or returning of the gel cards to the user. Three zones are arranged in said upper floor: one on the left for the reagents, diluents, samples and dilutions; one in the centre for the dispensing and incubation of cards; and one on the right containing the stored cards and the means of access to the centrifuges, the reader and the scrap card area. For controlling the operations necessary for an analysis, the apparatus has two movable heads in the upper floor, with the movements along both X-Y axes covering the whole of the assigned zone in the upper floor. The heads themselves do not require any movement along the Z axis. However, some individual elements of each head do have the ability to move along the Z axis, such as the sample-tube stopper perforating device and the mechanism for moving the gel card holding clamp, as well as others that will be explained.

Therefore, both heads are located at the same working compartment; the liquid-handling head requires access only to the left zone and the central incubator zone, while the card-handling head requires access only to the right zone described above and to the central incubator zone. Both heads can therefore perform the corresponding necessary tasks independently and simultaneously without interfering with each other, except in the incubator zone. To this end, the guide systems of the heads and the design of the same permit that when the liquid-handling head performs any operation in any position in the left zone (regardless of the position of the rack and the dilution well), it does not impede the access of the card-handling head to any of the cards in the incubators (including those located more to the left according to the configuration example), and complementary, when the liquid-handling head moves to dispense any card located in an incubator (including those located more to the right), it does not impede the access of the card-handling head to any of the elements of the right zone, including the card scrapping slot.

For the pipetting of samples and reagents and the movement of cards, the apparatus has, as indicated above, two movable heads in the upper floor, running on upper guides to allow their individual movement in the longitudinal and transverse directions, along two coordinate axes X,Y.

The apparatus has two centrifuges, which are arranged beneath the card drawers, and a card reader.

The upper floor of the apparatus has various interchangeable supports for reagents, diluents and samples.

In one example, the reagent supports consist of two removable racks, each housing one of the two different sub-racks, one intended for reagents that must be agitated (17 positions) and the other for diluents (1 position) and reagents that do not have to be agitated (5 positions).

The removable reagent racks are provided with an agitation mechanism for vials that must be agitated, with magnetic eccentricity for orbital motion and driven by a magnetic-clutch motor located beneath the rack-holding platform. The reagent racks have a magnetic guidance/braking system, as well as a magnetic system for detecting the type of rack and a fastening system, as will be explained later.

In one example, the sample supports also allow the samples to be inserted by means of removable racks, each drawer housing two identical interchangeable racks, each of which allows the insertion of 12 samples. In a manner similar to the reagent racks, the sample racks have a magnetic guidance/braking system, as well as a magnetic system for detecting the type of rack and a fastening system, as will be explained later.

In addition to the magnetic guidance/braking system, each reagent and sample rack has a magnetic system for detecting the type of rack, and each individual housing has a strap for holding each vial or tube individually in its housing. The detection of the type of rack is carried out by means of a double magnetic field sensor, combined with a magnet positioned in the sample or reagent rack. The different position of the magnet in each type of rack makes it possible to detect the type of rack in the machine. Guidance and braking are achieved by the provision of matched sets of magnetic strips of different polarity both in the base of the upper floor of the apparatus, on which the racks are moved, and in the lower base of the rack itself, in which the magnetic strips are arranged with opposite polarity so as to mate with the strips in the floor of the apparatus. In this way, the insertion and removal of the racks are guided magnetically by the interaction of the magnetic strips, without any need for physical guides such as profiles, tabs, etc. This is advantageous from the point of view of permitting the creation of a completely smooth floor for receiving the racks, thus allowing, in addition to great constructional simplicity, effective and rapid cleaning whenever this is necessary.

Each rack also has a magnetic fastening system, such that the insertion of the rack in the resting position in the upper floor entails the insertion of a rack locking pin. To open the rack, the user must request this operation via the electronic controller of the apparatus. This gives a high level of handling safety.

The upper floor is also provided with a dilution well, which allows the blood samples to be diluted without the use of disposable elements, being equipped with a washing system. To homogenise the dilution, the well assembly is provided with an orbital agitation system consisting of a motor-driven magnetic eccentric mass with magnetic clutch located beneath the well-holding platform.

As already mentioned, the upper floor of the apparatus houses two moving heads which have all the suspended connections necessary for its movement along the X and Y axes. This makes it possible to optimise the available surface area in the upper floor of the apparatus. Each head can access the entire surface of its respective floor, without any dead zones.

The pipetting head contains two probes, one for the pipetting of samples and reagents and one for perforating the stoppers of the sample receptacles, as well as a system for identifying barcodes and detecting the presence of samples, reagents and diluents.

The pipetting probe has a capacitance level-detecting system and a system for detecting correct pipetting. The capacitance system detects the level of liquid in the tube, which will serve as a reference for calculating the penetration height of the aspiration needle in order to achieve the volumetric characteristics determined by the electronic controller of the apparatus. The system for detecting correct pipetting is intended to detect any problem in the pipetting operation that might give rise to a pipetting defect, for example a partial blockage due to clots, etc., which will also be reflected in the electronic controller of the apparatus so that the operator can be aware of this fact and take the necessary measures. The probe passes through a washing system that allows the internal and external washing of the probe.

A sample and reagent identification system is incorporated into the head, with a laser proximity detector which allows detection of the presence and diameter of sample tubes and detection of the presence of vials/bottles of reagents/diluents in the racks. This detector is located in a fixed position in the base of the head. A barcode reading system is also provided, with a structure that moves vertically relative to the head. Within this structure are housed two barcode readers which, by means of mirrors, are capable of reading in opposite directions. The width of the structure allows it to be lowered with the head situated above a rack, in such a way that the beams of the barcode readers are directed at the tubes/vials/bottles.

Three incubator blocks arranged in line, again in the upper floor of the apparatus, are intended for incubating the cards at a controlled temperature, for example between 24° and 37° C.

The incubator unit is made of aluminium to allow good heat transfer, and has two housings for inserting the cards. The reaction chamber zone and the card microtube are covered by the incubator unit.

Temperature regulation is achieved by means of a Peltier cell and two temperature sensors.

The incubators have multiple modules with slots for receiving cards and heating/cooling elements using Peltier cells, said modules being integrated by means of aluminium elements in contact with the Peltier cells.

Also situated in the upper floor of the apparatus are the drawers for the cards, which allow the cards to be inserted in their original manufacturing holders, each drawer being capable of housing 4 holders. The drawer is screwed to a metal sheet base and is supported by two linear guides that provide rigidity once opened. The opening of the drawers is achieved by means of an electric security closer, in such a way that the drawers must be opened by submitting a request to the electronic controller that controls the apparatus.

The centrifuges are arranged beneath the card drawers, each with various independent tilting holders that allow the centrifugation of the cards in the axis of the wells.

The top cover has an opening that allows the card transport system to place each card in a holder. The top cover also holds the motor that imparts the rotation.

In the centrifuge, the rotor is attached to the motor shaft. In one example, it has twelve housings for the holders.

The reader is located beneath the first card drawer and has an opening in its cover that allows the card transport system to insert a card so that it can be read.

The card transport head is also located in the upper floor and has a rectilinear movement along the X and Y axes, with suspended connections to optimise space use and allow access to any of the intended zones of the upper floor. The head has a clamp and a card identification system.

The lower floor of the apparatus is provided with housings for solutions, especially two different solutions, as well as two housings for waste liquids and one housing for scrapped cards. The four liquid housings are identical to each other, and the one intended for the cards receives a container instead of drums.

The housings are supported by means of linear guides parallel to each other, and a weighing system with a strain gauge is used for checking the quantity of liquid in the drums or the quantity of cards in the scrap drawer.

Behind and to the right of each of said housings is located the fluidic system and its electronic controller.

The electronic control system of the apparatus is located beneath the centrifuges in a metal drawer that houses the bulk of the electronics, the power source and the control computer.

The fluidic control unit is contained in a methacrylate block in which the pressure sensors, pumps and tubes are connected with an electronic control plate.

The card drawers are attached to a metal sheet base shared with the centrifuges. This base is hinged at its rear and supported by several hydraulic springs to provide maintenance access to its lower portion, as well as to the electronic and fluidic control components located beneath the base.

The base that supports the sample and reagent inlets, as well as the dilution well and the reagent and well actuation motors with all their electronics, is hinged at its rear and supported by a hydraulic spring to provide maintenance access to all the components located beneath the base.

The apparatus has a touch screen supported by a mechanical arm that allows it to be pivoted to suit the user's convenience, the user being able to enter parameter values, read information and warnings, and generally interact with the apparatus. It is also provided with a front push-button panel for opening the reagent and sample racks and the gel card drawers.

To allow a clearer understanding, by way of explanatory and non-limitative example, some drawings are attached of a preferred embodiment of the present invention.

BRIEF DESCRIPTION OF THE DRAWINGS

FIG. 1 bis shows a view with the left part of the apparatus raised up on its hinges for maintenance and servicing.

FIG. 4 bis shows a transverse cross-section of the right side, for the cards, of the upper floor.

FIG. 5 bis shows a view with the right part of the apparatus raised up on its hinges for maintenance and servicing.

FIG. 14 bis shows a transverse cross-section of a rack of reagents.

FIG. 18 bis shows a plan view with partial cross-section of the gel card incubator device.

DETAILED DESCRIPTION

Figure 1:
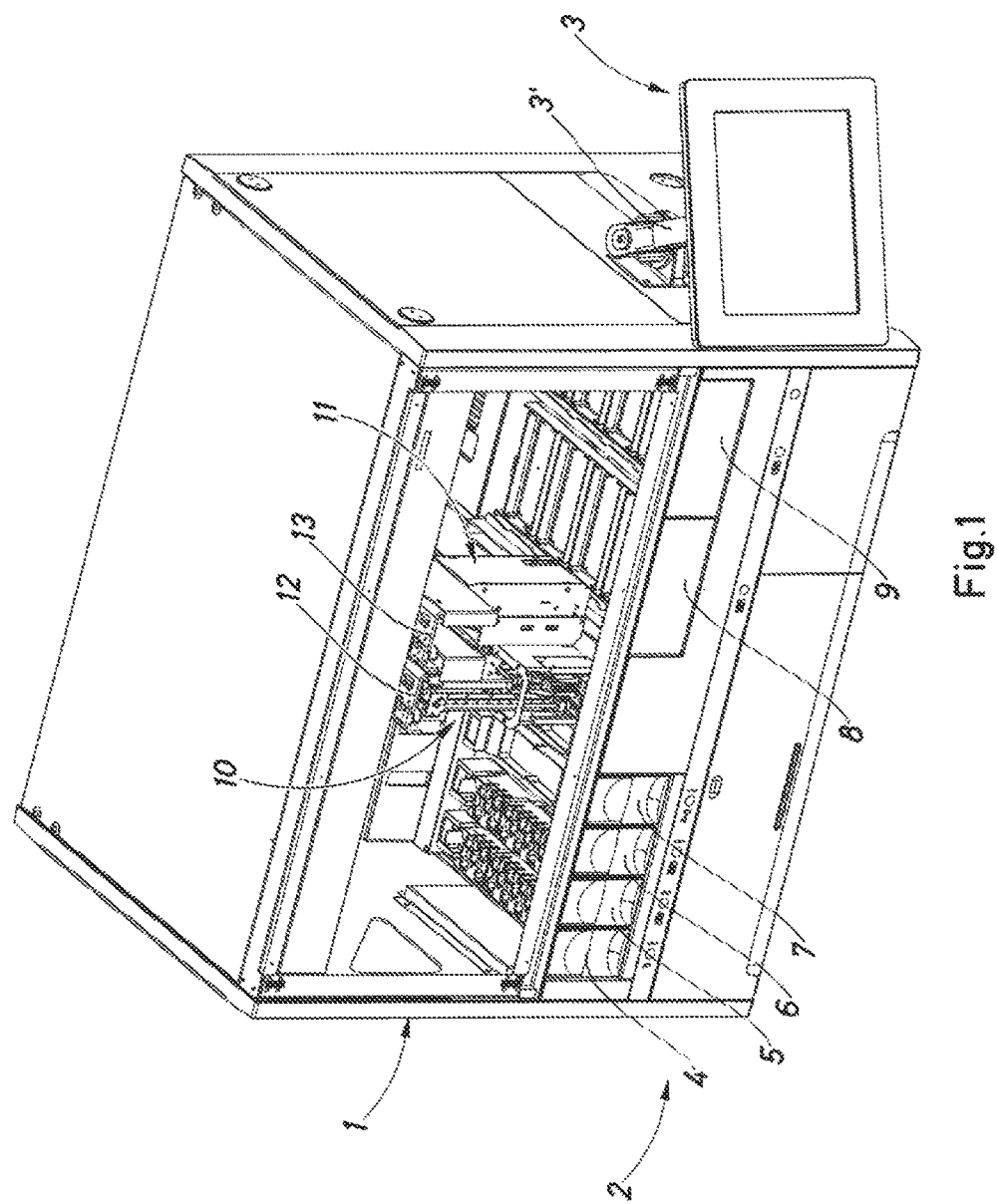
FIG. 1 shows a perspective view of the apparatus and the touch screen.

Numerous devices are known in the state of the art for the conduct of immunohaematological tests, in particular for the analysis of blood samples on gel cards, such as that described in the present applicant's own patent no. 09380082.

This type of machines must handle the samples, reagents, diluents and gel cards, among other elements. The set of components for the storage of the different products and samples and for the performance of the complete analysis process involves substantial mechanical complication, providing the mechanical components for the different functions as well as the electronic components for controlling the different maneuvers in order to carry out the series of operations involved in an analysis process, read the results and present the same in a way that is useful for the operator.

The mechanical, electronic and fluidic complexity of these devices has, until now, represented a major complication and costliness in their operation. This impedes the proper extension of automatic immunohaematological analysis devices to different medical centres of smaller size, and also limits the provision of the current devices to a few specific locations within a large clinical facility.

As has already been explained in the applicant's earlier patent, these diagnostic techniques require a series of handling operations, some of them (a) relating to the handling of liquids (identification of reagents, diluents and samples, dilution and pipetting of samples, reagents and dilutions in the gel cards), and others (b) involving the handling of gel cards (identification, selection and transport of the necessary cards, incubation of the cards once they have been pipetted, and transfer of the cards to the centrifuges and the reader, and finally the scrapping or retention of the cards for subsequent re-use). In a similar way to the previous patent, the machine is provided with two heads, one for each group of tasks (a) and (b) described above. However, these groups of tasks overlap with each other, since during the card handling tasks (b), the cards must be temporarily available so that the head that performs the tasks (a) can dispense on to them the liquids required for the analysis process. In a similar way to the previous patent, it has been considered convenient for the dispensing on to the cards to be carried out in the same place where the incubation of the cards will take place if required, in other words the incubators are a shared resource for the heads in the performance of the tasks (a) and (b). In the earlier patent, the tasks (b) are carried out in a lower compartment or level of the apparatus, while the tasks (a) are carried out in an upper compartment or level, and to this end the incubators have capacity for vertical movement for moving from the lower compartment for the tasks (b) to the upper compartment for the tasks (a), before returning to the lower compartment to continue the tasks (b).

To solve the problem described above, the inventors have proposed the construction of an apparatus for the automatic testing of blood samples with new features that will make it possible to obtain an apparatus of reduced dimensions and weight, with a significant organic simplification and a lower overall cost, allowing it to be installed and used in different areas of a given hospital or in smaller facilities. In addition, given the dimensions and weight of the apparatus, it can be easily moved from one area of the clinical facility to another, or between different facilities if necessary.

The apparatus forming the subject of the present invention is formed of a single body that is easily handled and usable in a benchtop arrangement, in such a way that all the components are essentially at the height of the operator in a seated position. In FIG. 1 can be seen the box-shaped body of the apparatus, which comprises an upper operating floor —1— in which are arranged the functional components of the apparatus and a lower floor —2— in which are arranged the containers for washing solutions, waste liquids and the collection of used cards, as well as the electronic control system of the apparatus and the fluidic control system intended particularly for the control of washing fluids.

A folding touch screen —3—, with an articulated arm —3'—, allows the operator to interact with the apparatus by receiving information and entering instructions or functional requests.

As can be seen in FIG. 1, various supports or drawers for reagents and samples are incorporated in the left part of the upper floor —1— of the apparatus. This drawing shows an example arrangement in which the supports —4— and —5— allow the housing of racks of reagents and diluents and a further two supports —6— and —7— are designed to house the sample receptacles. It should be noted that the apparatus is designed for interchangeability of the positions of the reagent, diluent or sample racks in any of the supports. In other words, without any limitation whatsoever, the operator could have, for example, a single support for reagents and diluents and the others for samples, or alternatively could use two or three supports for reagents and diluents, bearing in mind that preferably two positions will be fitted with agitators intended for the vials of reagents.

In the right part of the upper floor of the apparatus are shown two drawers —8— and —9— for racks of cards. Said racks in their commercial implementation may be arranged directly in the different housings provided in said drawers.

With the ability to move over the indicated zones of supports for racks of different types and cards, the apparatus has two heads —10— and —11— respectively for the perforation of tubes with stoppers and the pipetting of liquids and for the handling of the gel cards. Said heads are mounted on respective carriages —12— and —13— which can be moved in the longitudinal direction of the apparatus along guides that run in the upper part of the apparatus, which are not visible in FIG. 1 and will be explained in more detail later. Similarly, the heads —10— and —11— can be moved on transverse guides of the carriages —12— and —13—, in such a way that said heads can be moved without any impediment over any point of the upper floor in the zone corresponding to each head, i.e. the head —10— in the whole of the zone for racks of reagents, diluents and samples and in the card pipetting zone, and the head —11— over the gel card drawers, incubator, centrifuge filling windows and others, which will be explained.

FIG. 1 bis shows the tilting nature of the part —10'— of the upper floor intended for reagents, diluents and samples, as well as the dilution well. The tilting is achieved by means of hinges in its rear part, and allows easy access for maintenance, cleaning, etc.

The front door of the apparatus can be opened as a whole, for example in a guillotine manner.

Figure 2:
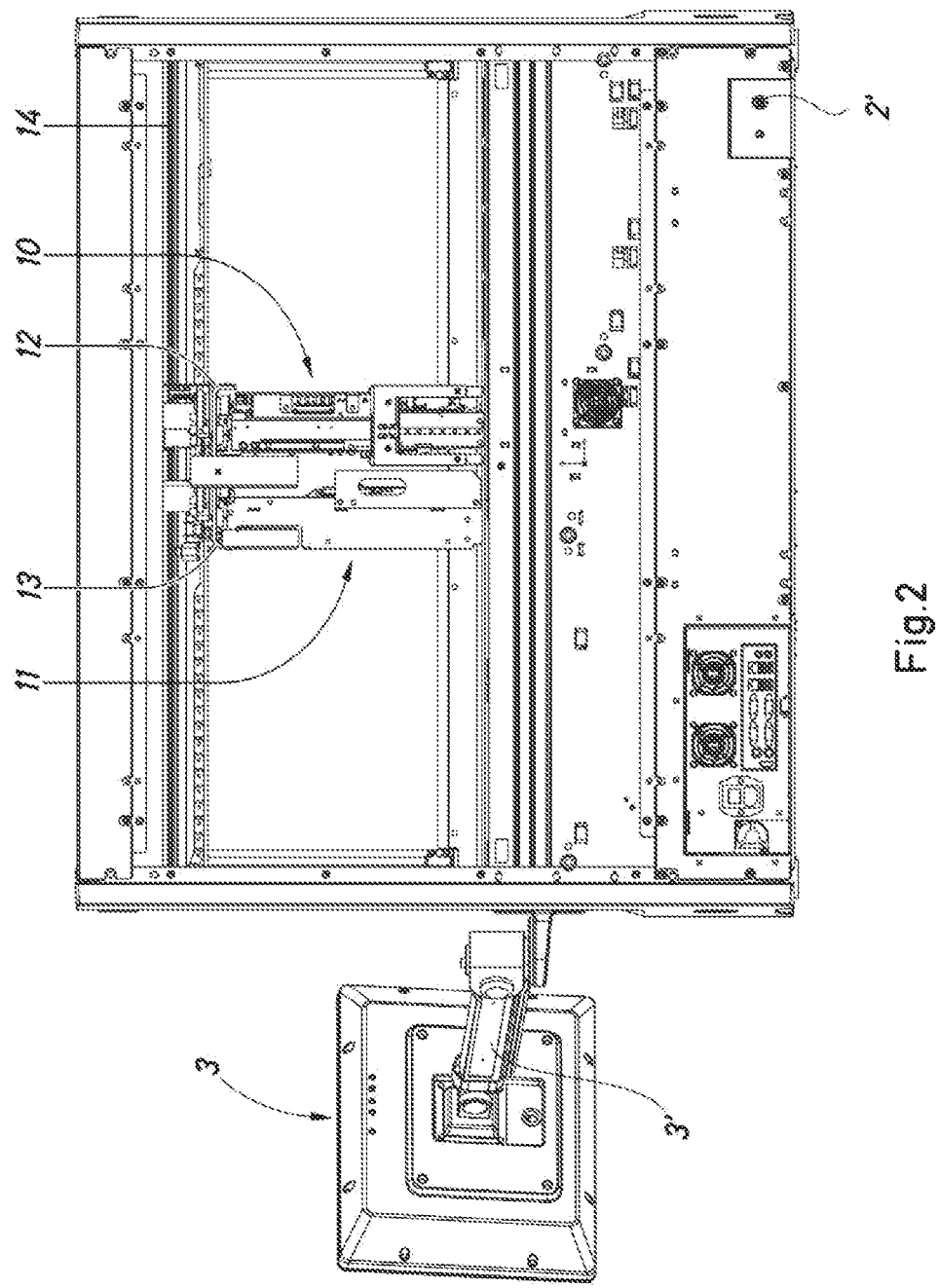
FIG. 2 shows a rear elevation view of the apparatus with the back cover removed and the touch screen.

FIG. 2 shows a rear elevation view of the apparatus in which can be seen the heads —10— and —11— with their upper supporting carriages —12— and —13, as well as the upper longitudinal guide —14— along which the carriages —12— and —13— are moved.

FIG. 2 also shows the touch screen —3— which, by means of the articulated arm —3'—, can be positioned folded against one side of the apparatus or in the unfolded position, as shown in said FIG. 2. This latter position corresponds to the working position of the apparatus, in which the operator can interact with the screen.

Figure 3:
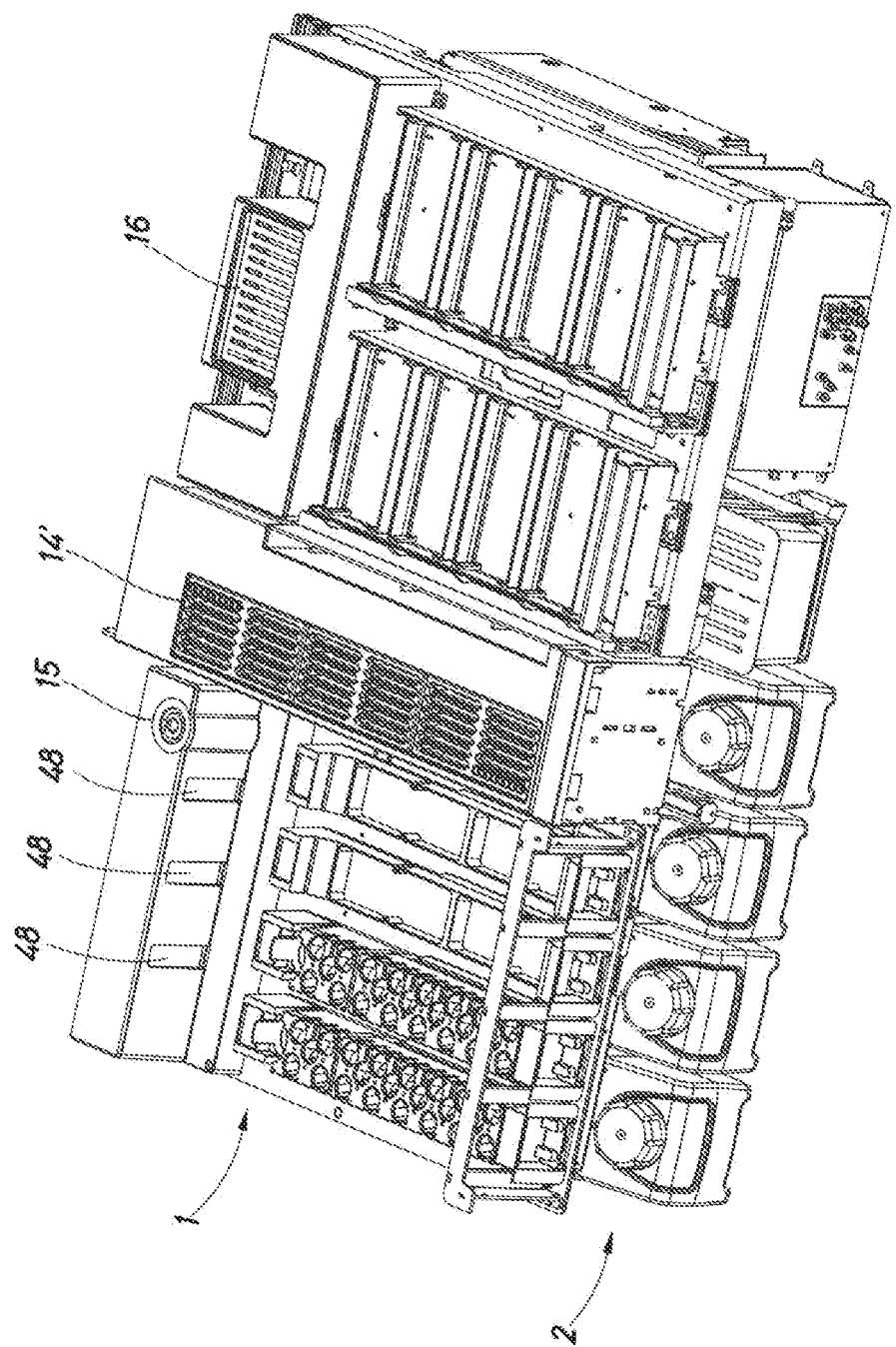
FIG. 3 shows a partial perspective view of the apparatus in which the top part of the upper floor can be seen.

In FIG. 3 can be seen the base of the upper floor —1—, with part of the components already described and also the set of incubators —14'— arranged between the reagent and sample zone and the gel card zone, in order to keep the cards at a controlled temperature. FIG. 3 also shows the dilution well —15—, in which blood samples are diluted without any disposable items, and a support —16— for cards that have only been partially used, i.e. in which some of the wells have not yet been used. In the plan view of Figure can be seen the components described above of the upper floor, as well as the arrangement, by way of representative example, of two gel cards —17— and —18— in the incubator zone, as well as a further two gel cards —19— and —20— in the positions that correspond to the windows for transferring the gel cards to the centrifuges, located beneath the floor plate of the upper floor. Also visible is the opening —20'— for access to the card reader located underneath. Also visible is the opening —20"— for sending cards to the scrap bin.

One of the features of the apparatus forming the subject of the present invention lies in the construction of the base or floor plate of the upper floor, in the part that corresponds to reagents, dilutions and samples, which is smooth and impermeable with respect to the assembly of mechanisms located beneath said floor plate, so as to avoid any possibility of contamination of mechanical and electric or electronic parts and simultaneously facilitate the cleaning of said floor plate. To achieve this effect, the apparatus forming the subject of the present invention is characterised by the magnetic interconnection between the motors located in the lower floor and the components intended to be driven in the upper floor. Said base or floor plate is also provided with magnetic elements for guiding and braking the supports or drawers carrying the racks of reagents and diluents, as well as those intended for supporting the sample receptacles. All of this will be explained in more detail below.

Figure 4:
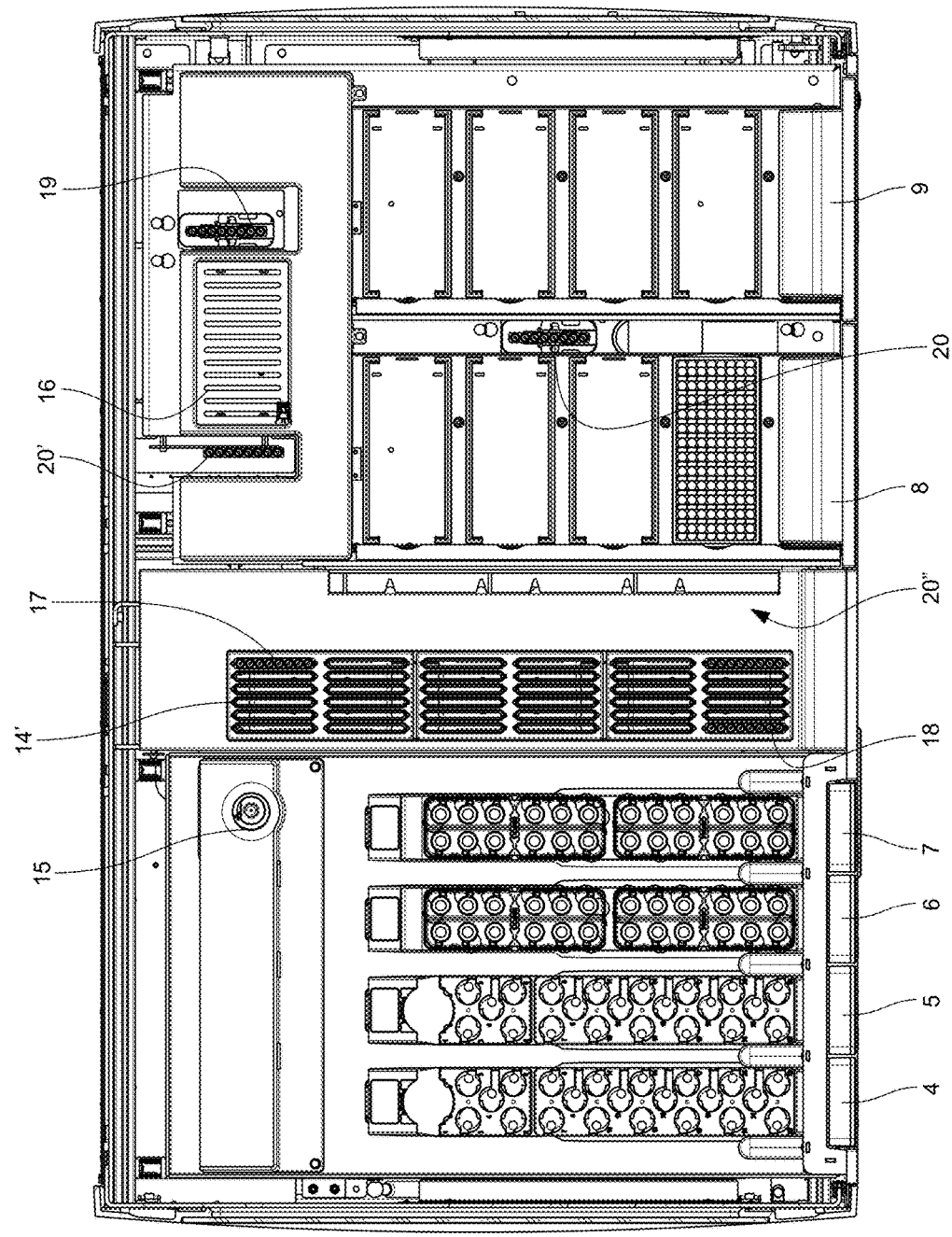
FIG. 4 shows a plan view of the upper floor of the apparatus.

FIG. 4 bis shows a cross-section of the part corresponding to the cards, showing card holders —20'— that are held in the working position by the end lugs of the holder, which are retained, respectively, at one end by a flexible claw —9'— of the drawer and at the other end by a fixed lug —8'—of the fixed structure of the upper floor. This arrangement keeps the card holders stable in their housing and facilitates their handling.

Figure 5:
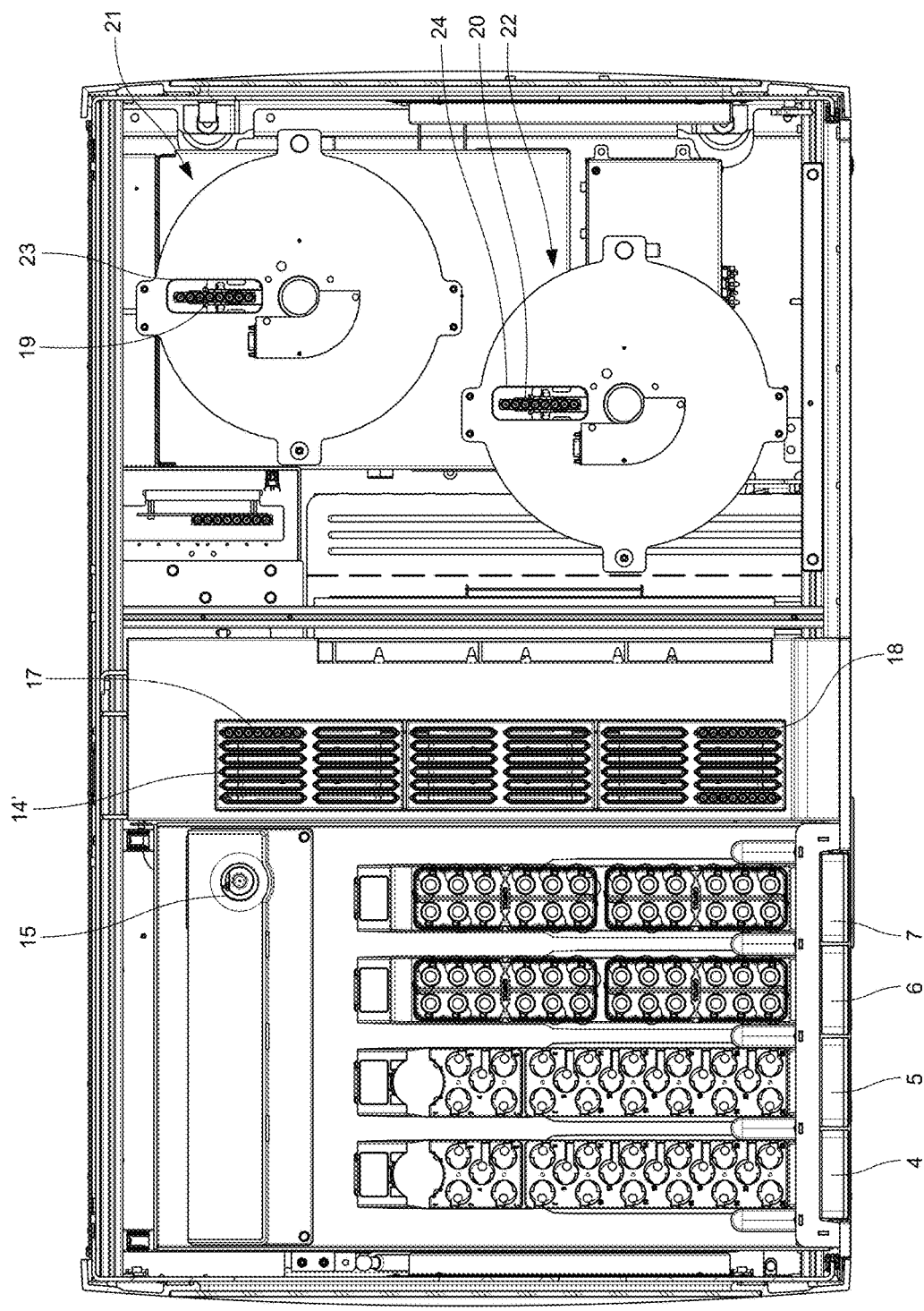
FIG. 5 shows a plan view of the upper floor of the apparatus in which the arrangement of the centrifuges and the other corresponding elements is represented schematically.

FIG. 5 shows a plan view of the upper floor of the apparatus in which the right side, i.e. the side corresponding to the gel cards, has been represented schematically, with the floor removed. In this representation can be seen the arrangement of the centrifuges —21— and —22—, which will be explained in more detail later. Said centrifuges are located beneath the floor plate of the zone intended for the gel cards, being arranged in separate closed containers provided with windows —23— and —24— for the insertion of the cards, which correspond to items —19— and —20— in FIG. 4.

FIG. 5 represents the tilting arrangement of the right part of the upper floor, in a manner similar to that represented in FIG. 1 bis for the left part.

Figure 6:
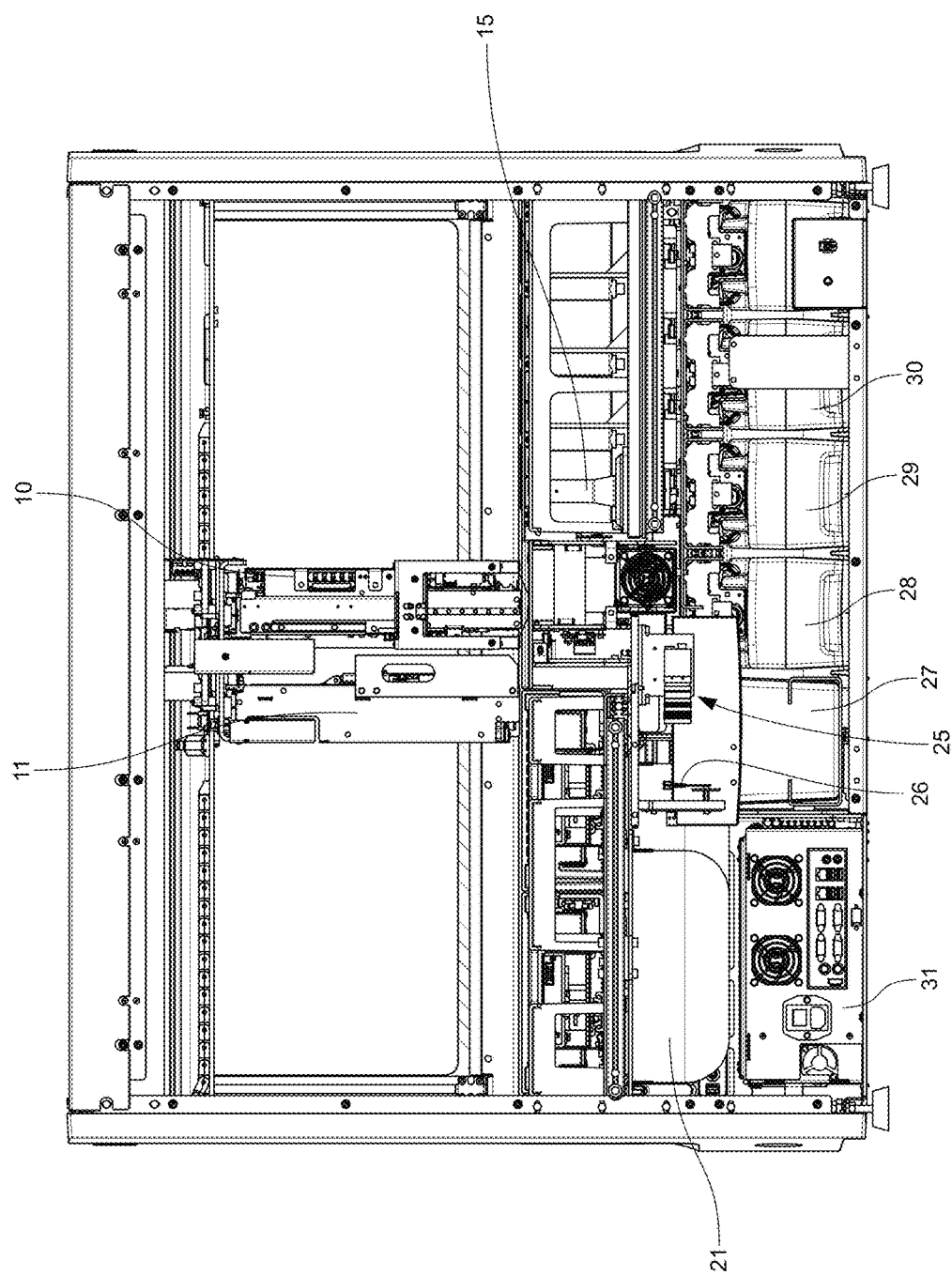
FIG. 6 shows a rear elevation view of the apparatus without back covers, in which the essential components of the upper and lower floors can be seen. The centrifuges and the reader are located underneath.

In FIG. 6, which shows a representative rear elevation view of the apparatus with the rear covers removed, can be seen the relative position of one of the centrifuges —21—, upper drawers for gel cards, dilution well —15—, and adjacent zone for the reagent, diluent and sample rack supports. Also visible in this view is the arrangement of the card reader —25—, in which a gel card —26— is shown schematically in the reading position.

In the same view can be seen part of the multiple receptacles of the lower floor such as —27—, —28—, —29— and —30— intended for liquids handled in the apparatus and any washing solutions, as well as a receptacle for scrap cards. A zone —31— is intended to contain the electrical and electronic components of the apparatus.

Figure 7:
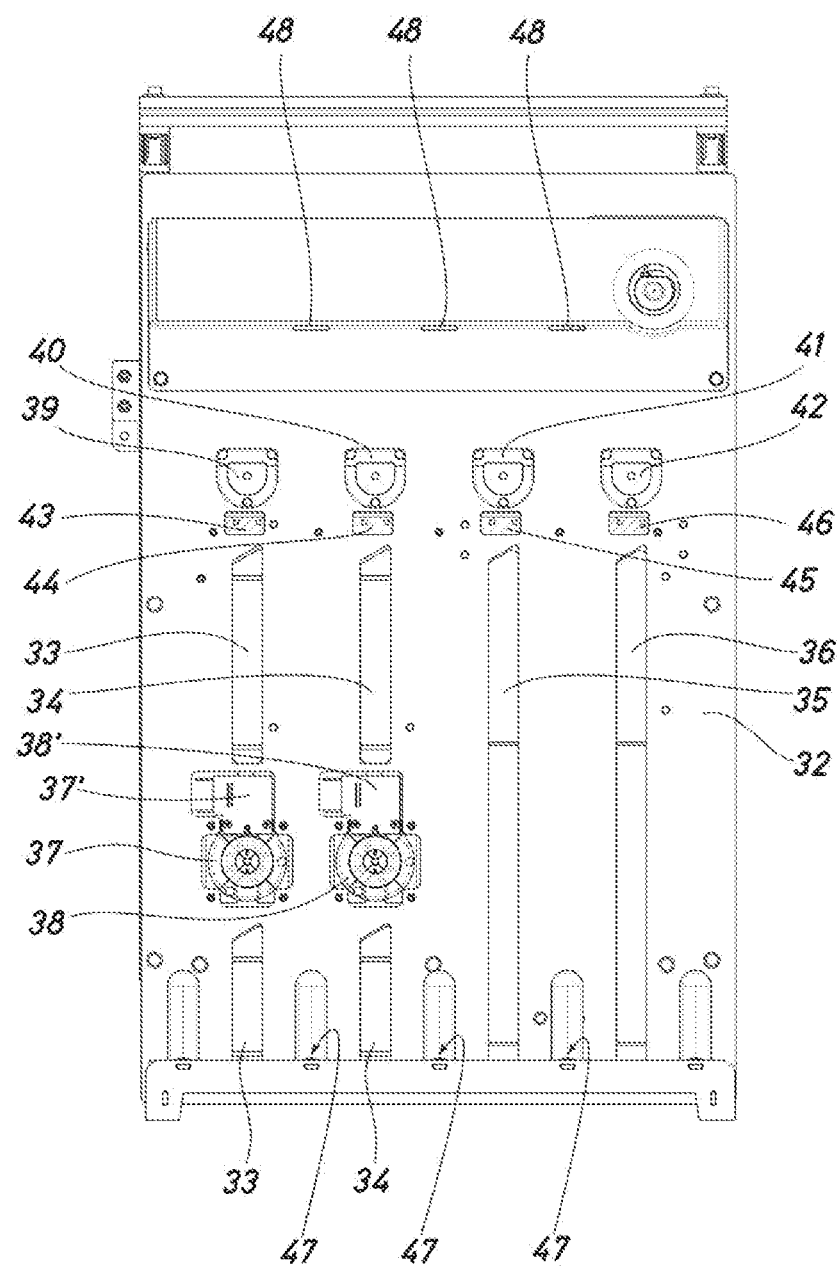
FIG. 7 shows a partial plan view without the cover of the first floor of the apparatus, representing schematically the magnetic strips for guiding and braking the racks, the rack detection sensors and the motors providing orbital actuation for agitation.

FIG. 7 shows a partial plan view of the zone of the upper floor that houses the reagent and diluent supports (—4—, —5—) and the sample supports (—6—, —7—). As mentioned previously, the base plate of the upper floor, which in this figure has been represented with the number —32—, is provided with a series of longitudinal magnetic strips such as those indicated with the numbers —33—, —34—, —35— and —36—. The magnetic strips are composed of adjacent strips of different polarity which mate with other strips located in the bottom part of the respective reagent and diluent supports (—4—, —5—) and sample supports (—6—, —7—), as will be seen later in FIGS. 13 and 17. In this way, the magnetic interaction between each removable support (for reagents and diluents or for samples) and the corresponding magnetic strips of the base plate —32— of the upper floor provides effective longitudinal guidance of each support within the upper floor when it is inserted, as well as providing braking for said support, avoiding vibrations in the containers of the different liquids arranged in the respective supports (for reagents and diluents or for samples).

Additionally, in the view of FIG. 7 can be seen the magnetic-clutch motors —37— and —38— for agitating the supports of racks of reagents that must be shaken. Said motors —37— and —38—, which are arranged beneath the plate —32—, allow, by means of magnetic coupling through said plate —32—, the agitation of the corresponding reagent racks without any possibility of liquid leaks. The reagent racks that must be agitated by said motors —37— and —38— will be described later in relation to FIGS. 11 to 14.

In the same FIG. 7 can be seen, along one side, a plurality of elements —39—, —40—, —41— and —42— for attaching the respective reagent and sample supports to the plate —32—.

Also visible are a plurality of sensors —43—, —44—, —45— and —46— for the magnetic detection of the type of reagent or sample support once said support has been inserted and arranged in its corresponding cavity in the plate —32—. As will be seen later, each reagent support and each sample support comprises a magnetic identifier that allows it to be correspondingly identified by the sensors —43—, —44—, —45—and —46— indicating the presence of one type of support or the other.

Figure 14:
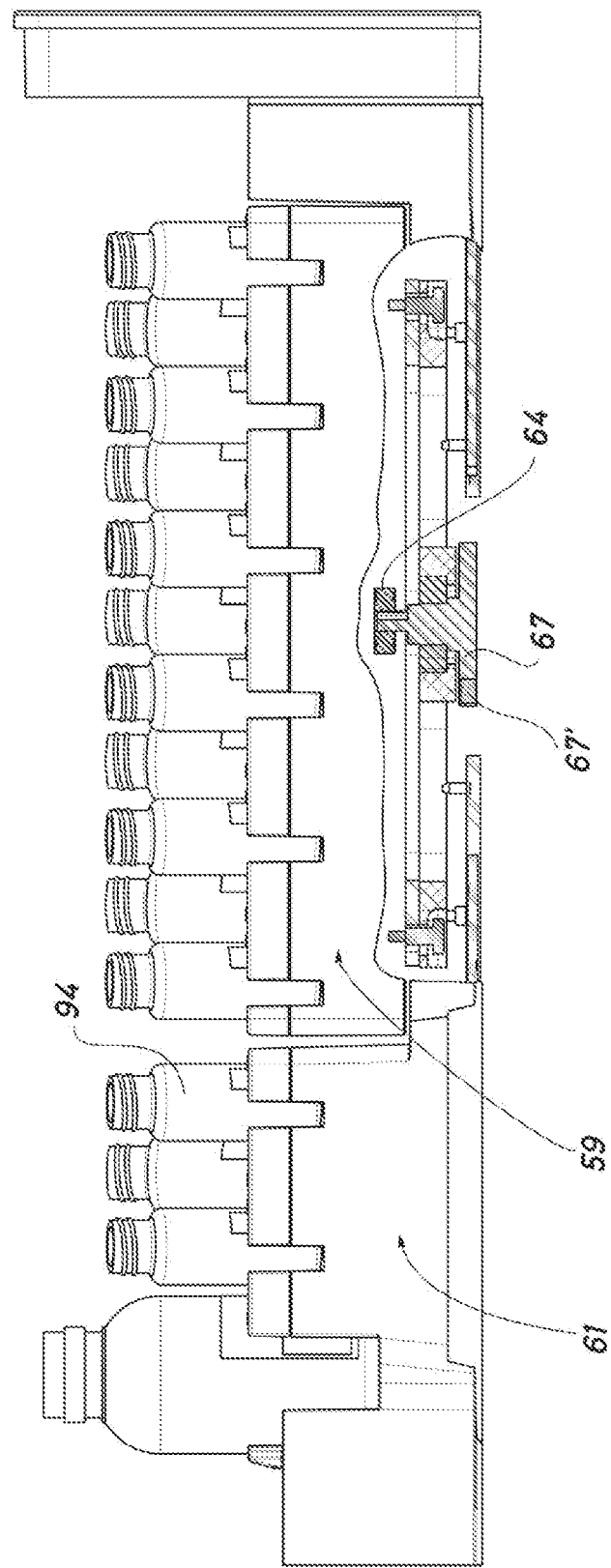
FIG. 14 shows a side and partial cross-section view of a rack of reagents, showing the actuation components for agitation.

Also visible in the same FIG. 7 is the provision of sensors —37'— and —38'— for controlling the movement of the reagent racks actuated by the corresponding motors —37— and —38—. Said sensors function in combination with rotating portions of the respective reagent racks, making it possible to detect whether or not the corresponding reagent rack is actually rotating. The functioning of said sensors —37'— and —38'— in combination with said rotating portions of the respective reagent racks, as illustrated in FIG. 14, will be explained in more detail later.

As illustrated in FIG. 7, the upper floor additionally comprises a system for detecting any improper intrusion of the user's hand or other similar object into any unoccupied cavity for reagent and/or sample supports during the operation of the apparatus forming the subject of the present invention. Said system comprises a plurality of infra-red emitters —48— located in the rear face of the upper floor and arranged in line with the spaces between the housings for each pair of adjacent reagent and/or sample racks. Said infra-red emitters —48— can also be seen in FIGS. 3 and 19.

Similarly, the front part of the upper floor is provided with a plurality of infra-red ray reflectors —47— respectively in line with each infra-red emitter —48—, in such a way as to allow the detection of any unpermitted intrusion during the operation of the apparatus. An example of unpermitted intrusion would be the hand of a user who, during the operation of the apparatus, wishes to reach from the front part of the apparatus through an unoccupied cavity for reagent and/or sample supports and improperly accesses the containers of reagents, diluents and/or samples in adjacent reagent and/or sample supports.

Figure 8:
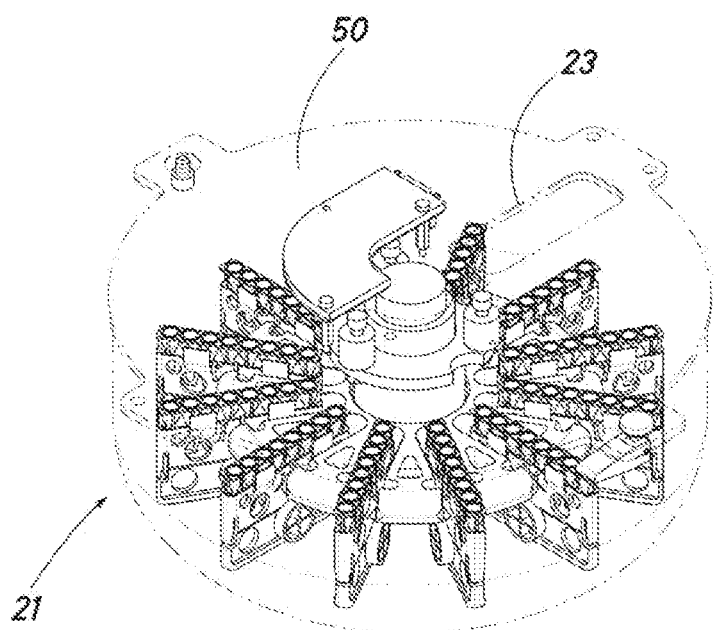
FIG. 8 shows a perspective view of a centrifuge.
Figure 9:
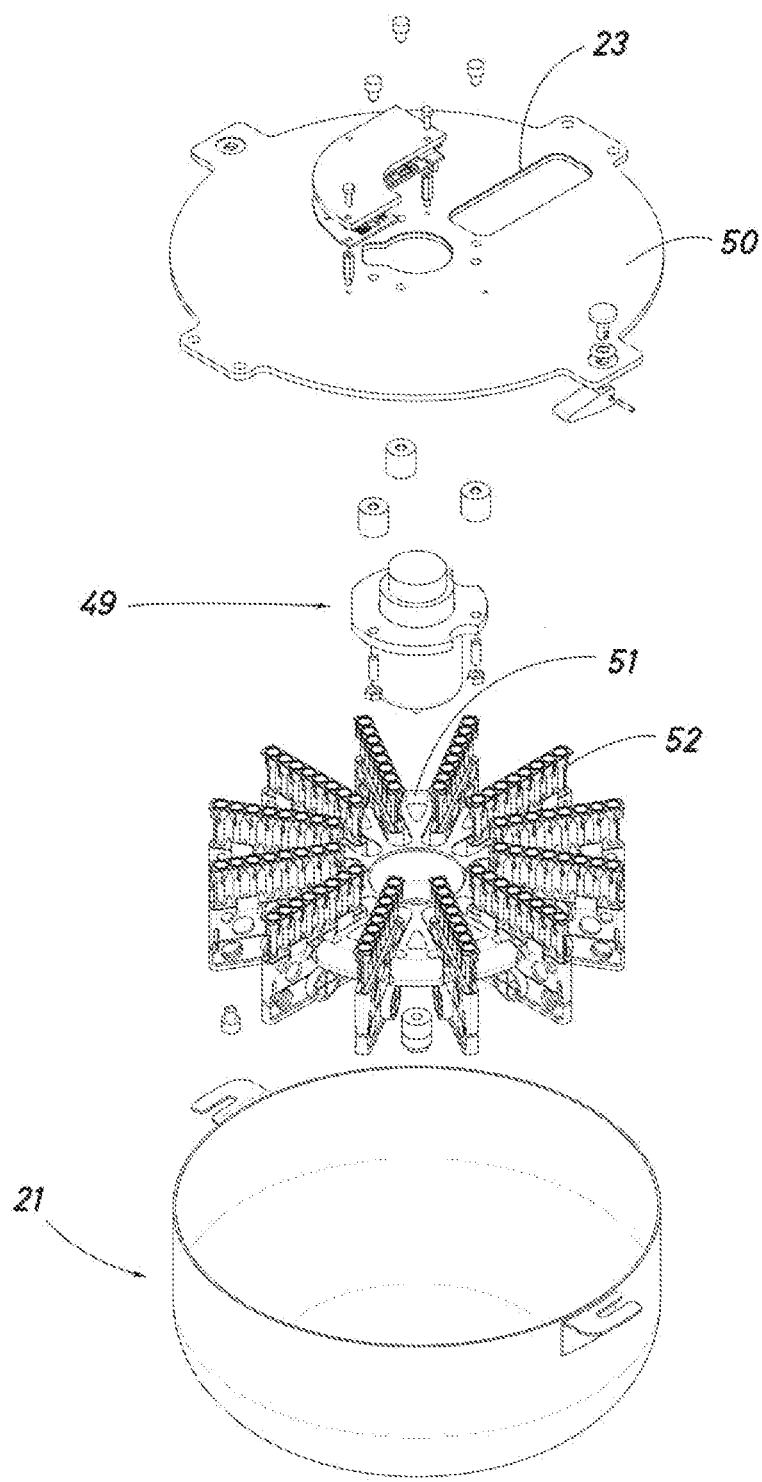
FIG. 9 shows a perspective view of a disassembled centrifuge, showing its essential components.

FIGS. 8 and 9 show a centrifuge, in the assembled position in FIG. 8 and disassembled into its main components in FIG. 9. The centrifuge —21— has a practically closed structure, with a window —23—, as explained previously, for the insertion of gel cards into the centrifuge, and is provided with a turning motor —49— and a top cover —50—. A rotor —51— is attached to the motor —49—, and said rotor carries individual tilting supports for the different gel cards —52—, which are loaded from above through the window —23— and which will remain with the wells in an essentially horizontal position during the operation of the centrifuge. In the embodiment shown, each of the centrifuges can house 12 cards.

Figure 10:
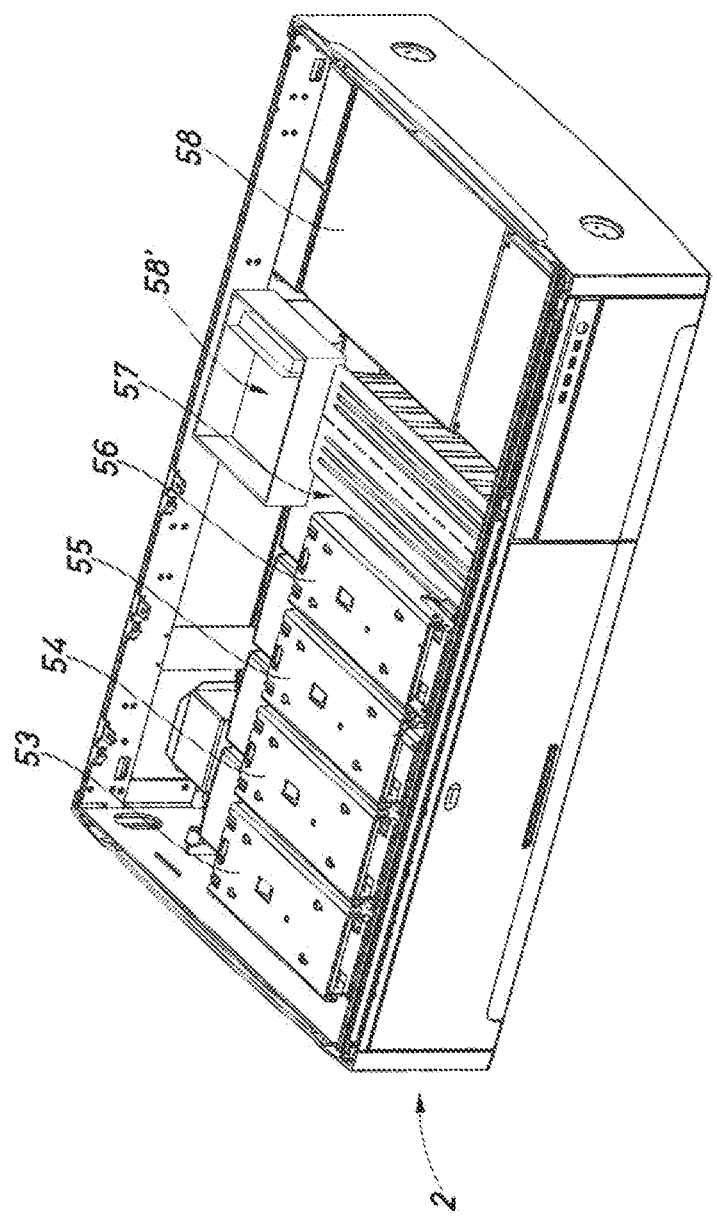
FIG. 10 shows a perspective view of the lower floor of the apparatus.

FIG. 10 shows the lower floor —2— which contains the housings for the washing solutions and for waste liquids and scrap cards. In the view shown, four identical housings —53—, —54—, —55— and —56— can be seen. In a preferred embodiment, solution A is for washing and solution B is for rinsing. In a preferred embodiment, the user can choose between two combinations, in one of which there is a housing —53— for solution A and a housing —54— for solution B, with the housings —55— and —56— intended for waste. In the second configuration, the housings —53— and —54— will be used for solution A and the housings —55— and —56 for solution B, with the provision in this case of an outlet —2'—, represented in FIG. 2, for conveying waste liquids to an external reservoir or drain.

The four housings intended for liquids are identical to each other.

In the same view of FIG. 10 can be seen the zone —58— for housing the fluidic system and its electronic controller, as well as the housing —58'— for the reader.

Figure 11:
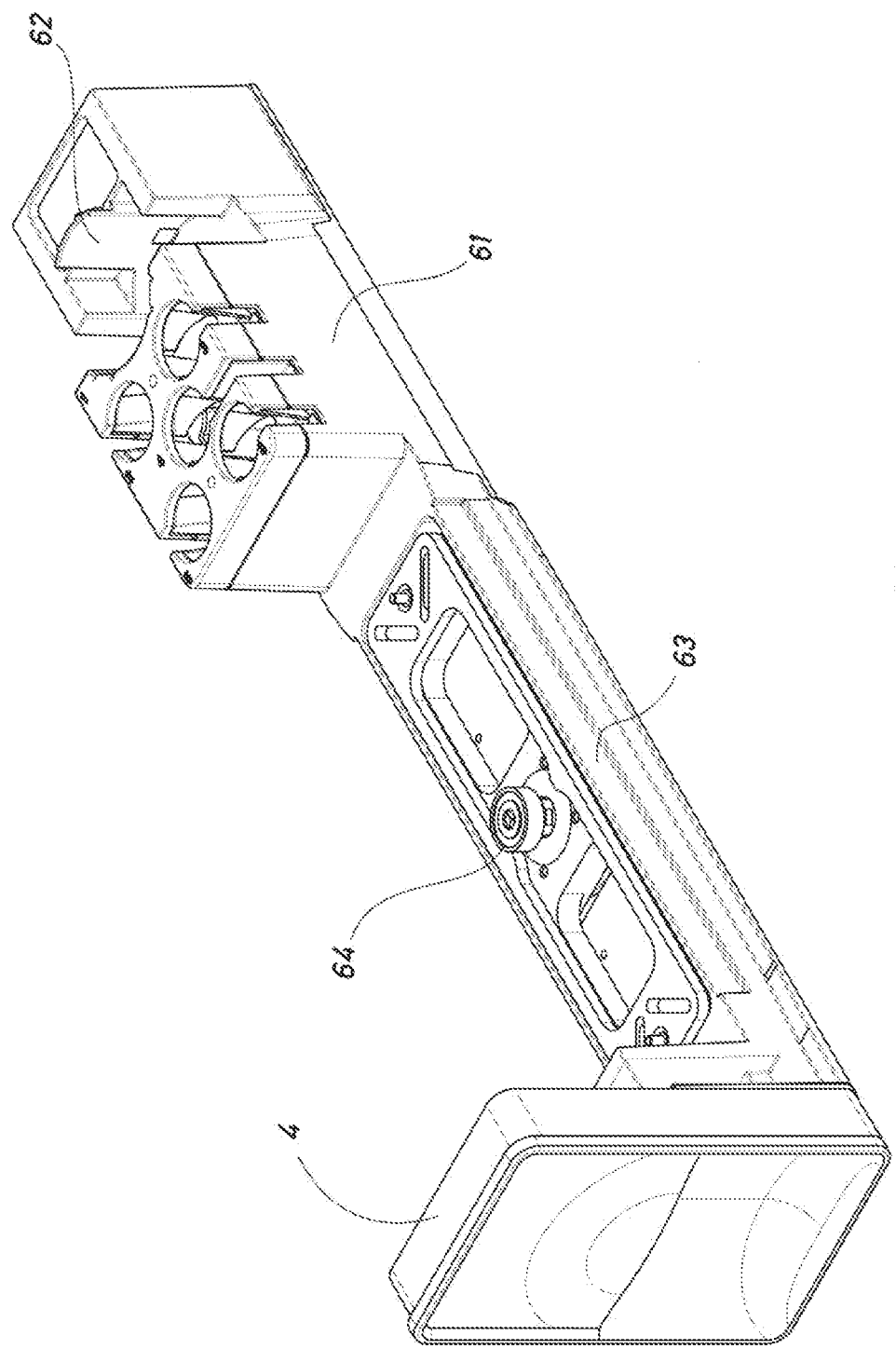
FIG. 11 shows a perspective view of the reagent rack support, showing only the rack for reagents which should not be agitated.
Figure 12:
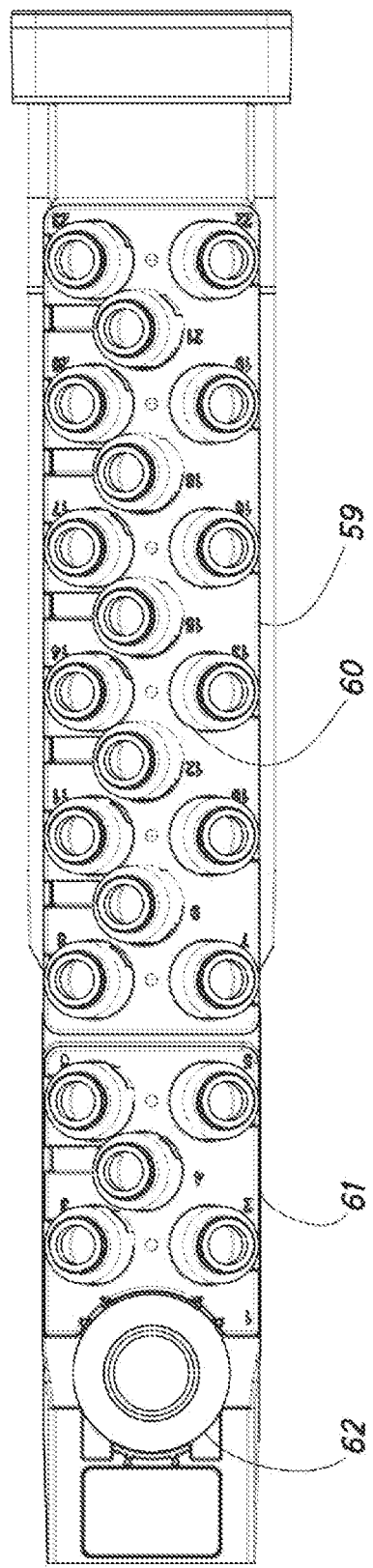
FIG. 12 shows a plan view of a support for racks of reagents and diluents.
Figure 13:
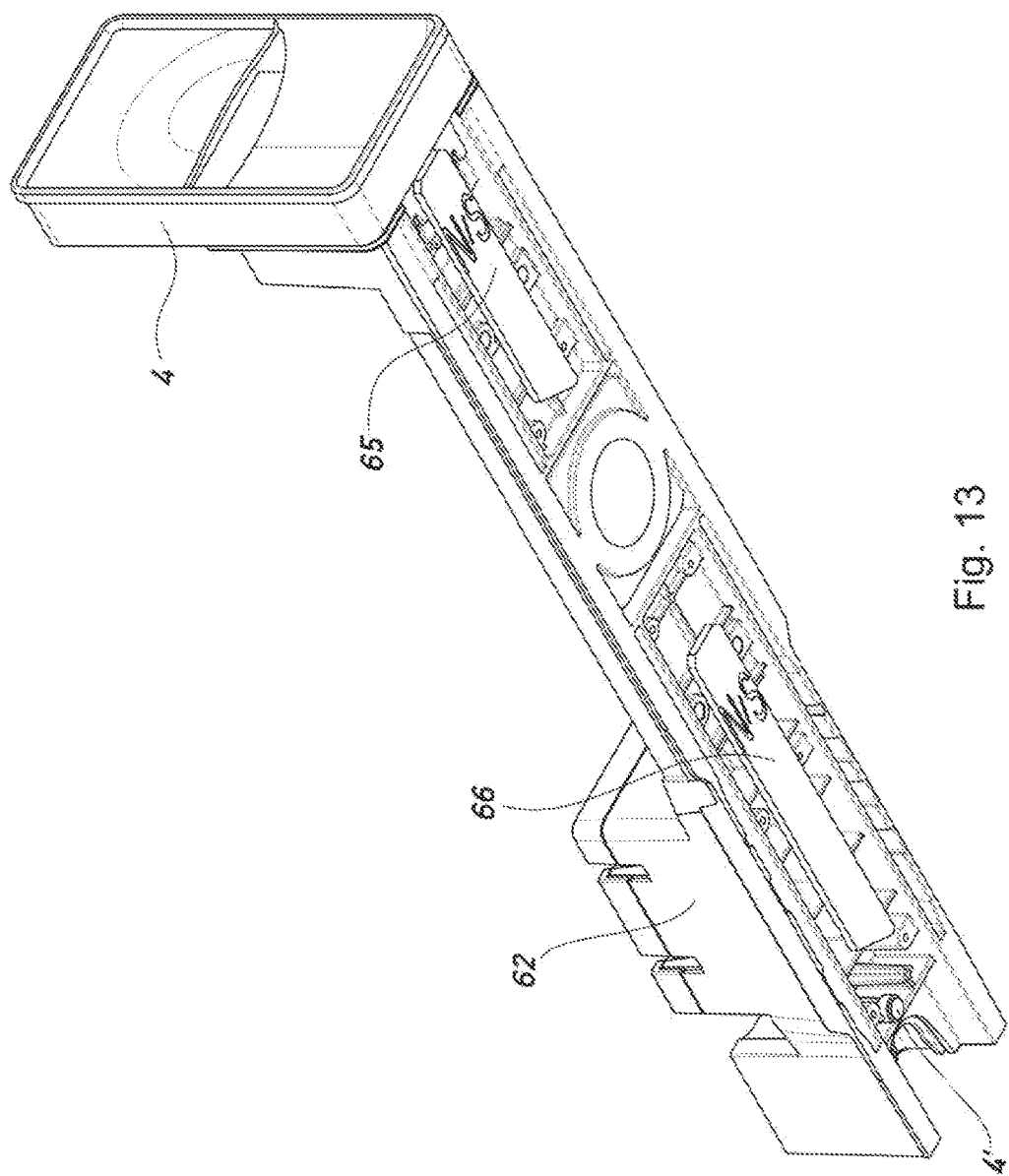
FIG. 13 shows a bottom view of the reagent rack support, showing the magnetic guidance and braking strips and the rack detection system.

FIGS. 11, 12 and 13 show respectively a perspective view, top view and bottom view of a support for reagent and diluent racks. For correspondence with the representation of FIGS. 1, 2 and 3, the support is indicated with the number —4—, which corresponds to the front handle. The support receives a first module or rack —59— of reagents, FIG. 12, which in the embodiment shown has 17 positions such as position —60—, said first rack —59— being intended for reagents that must be agitated, for which purpose it is combined with one of the motors (—37—, —38—) located beneath the base plate —32— of the upper floor, with magnetic coupling to produce the agitation. A second module —61— is intended for reagents that do not need to be agitated, and another housing —62— is intended to receive diluents.

In FIG. 11 can be seen the same support for reagent and diluent racks with the module 61— for reagents that do not have to be agitated and the base —63— for the rack of reagents that must be agitated (not illustrated). Said base —63— is subject to the action of the eccentric mass 64, which in turn is subject to the action of one of the motors (—37—, —38—) with magnetic coupling, located beneath the plate —32— of the first floor as shown previously in FIG. 7.

In FIG. 13 can be seen the lower part of the support for reagent racks, showing the linear magnetic strips —65— and —66— which work in combination with the corresponding linear magnetic strips —33—, —34— shown in FIG. 7. Additionally, the lower part of the support for reagent and diluent racks comprises an identifier —4'— for identifying the type of support. Said identifier 4'— is a magnetic element arranged in a specific zone in the lower part of the support in such a way that, when the reagent support is inserted into any one of the cavities for supports on the plate —32—, the respective sensors —43—, —44—, —45— and —46— explained previously in relation to FIG. 7 allow the detection by magnetic coupling of the type of support inserted.

FIG. 14 shows a representative view of the overall positioning of the support for reagent racks, illustrating the vials —94— with the module for reagents that must be agitated —59— and the module —61— for reagents that do not have to be agitated, as well as the agitating eccentric mass —64— and the driven disc —67— for actuating said eccentric mass by means of magnetic coupling with one of the motors (—37—, —38—) arranged beneath the base of the upper floor. Additionally, the disc —67— comprises a magnetic element —67'— arranged in an end zone of said disc —67—, which in combination with one of the sensors —37'— and —38' arranged beneath the plate —32— makes it possible to detect whether or not said disc —67— is being moved by the action of the respective magnetic-clutch motor (—37—, —38—).

When it is wished to carry out orbital agitation of the racks —59— of reagents to be agitated, the motors (—37—, —38—) with magnetic-clutch actuate by magnetic coupling the respective disc —67—, which in turn allows the orbital agitation of the eccentric mass —64— actuating the respective rack —59— of reagents to be agitated. In normal agitation operation, the respective sensors —37'— and —38'—detect whether the element —67'— is also being agitated. In the event of any blockage of the assembly (disc —67— and eccentric mass —64—), the respective sensors —37'— and —38'—would detect that the element —67'— has ceased to oscillate and that an anomaly has therefore occurred with said assembly (disc —67— and eccentric mass —64—) which prevents the agitation of the rack —59— of samples.

The vials —94— are arranged at a certain angle relative to the vertical, which allows better pipetting. The cross-section view of FIG. 14 bis illustrates the arrangement of the support, showing the inclination of the base —106— of each of the housings.

Figure 15:
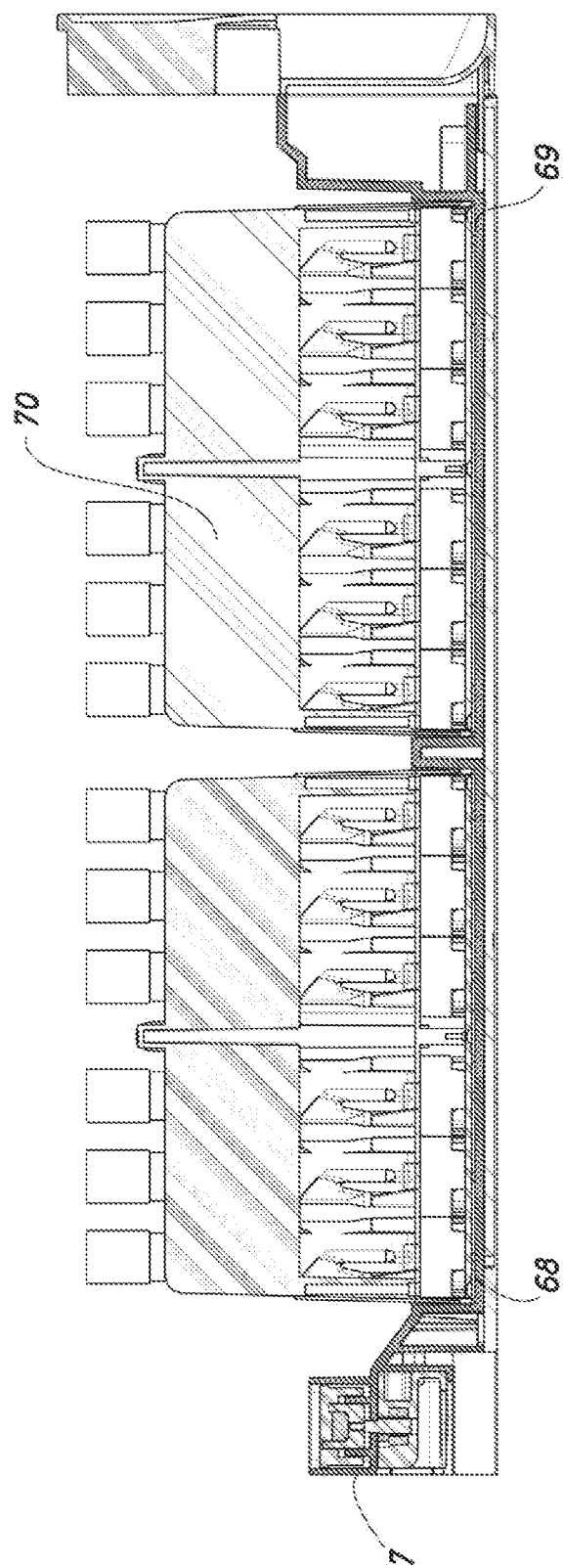
FIG. 15 shows a cross-section view of a support for racks of samples, with the racks in place.
Figure 16:
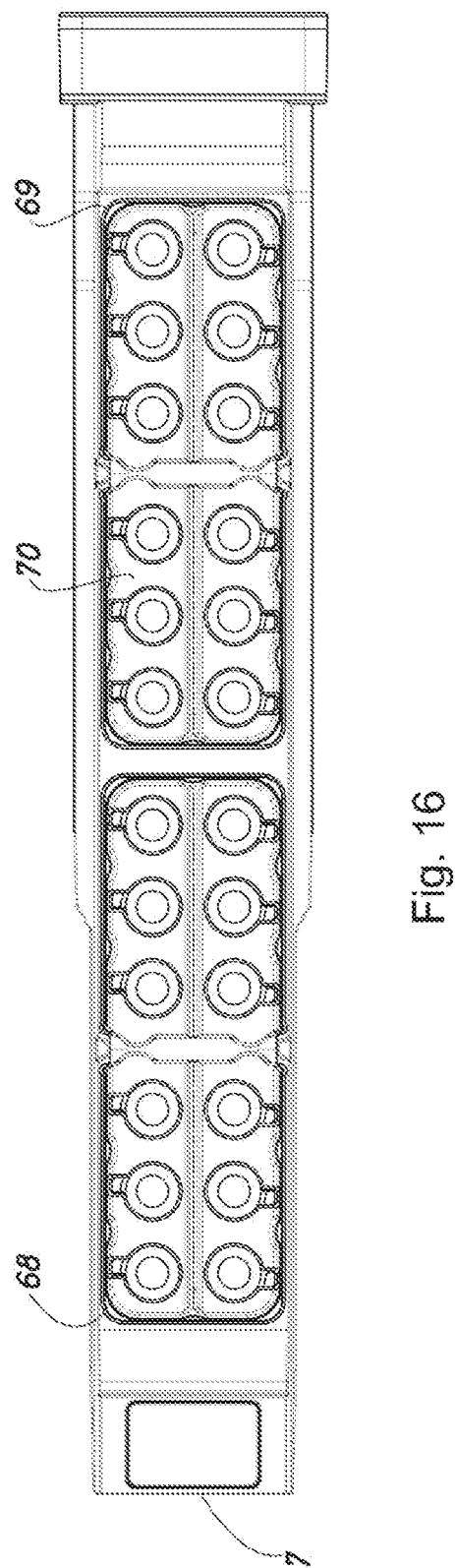
FIG. 16 shows a plan view of a support for racks of samples, with the racks in place.

FIGS. 15 and 16 show, by way of example, a support for racks of samples, with two racks in place. Said support is indicated with the number —7— for correspondence with FIG. 1, and in these figures it can be seen that the support is provided with two housings —68— and —69—, each for one rack of samples —70—, which in the illustrated example is intended to contain 12 tubes of samples. The supports are removable, in a manner similar to that described for the reagent supports, and are provided with a magnetic guidance and braking system and a system for detecting the type of rack, as well as a fastening system that will be explained in more detail later.

Figure 17:
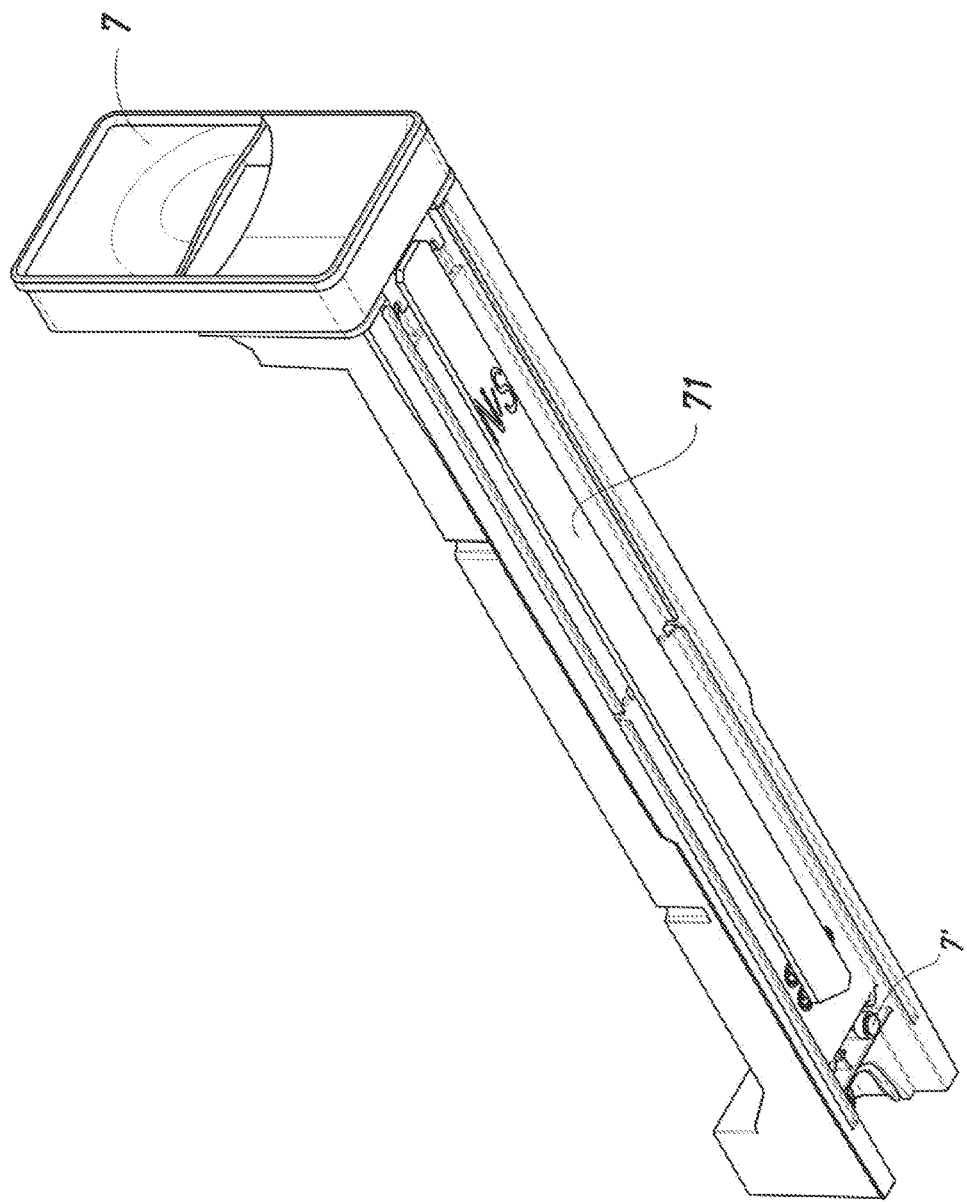
FIG. 17 shows a perspective view from below of the support for the racks of samples.

FIG. 17 shows a bottom view of the support for racks of samples, indicating the magnetic strip —71— which works in combination with the fixed magnetic strips, in a manner similar to that explained previously. Additionally, the lower part of the support for sample racks comprises an identifier —7'— for identifying the type of support. Said identifier —7'— is a magnetic element arranged in a specific zone in the lower part of the support in such a way that, when the sample support is inserted into any one of the cavities for supports on the plate —32—, the respective sensors —43—, —44—, —45— and —46— explained previously in relation to FIG. 7 allow the detection by magnetic coupling of the type of support inserted. Bearing in mind that, for the purposes of standardising the different types of support, the reagent and diluent supports —4— and the sample supports have the same dimensions, the identifier —4'— of the support —4— for racks of reagents and diluents will have a location different from that of the identifier —7'— of the sample support —7—.

Figure 18:
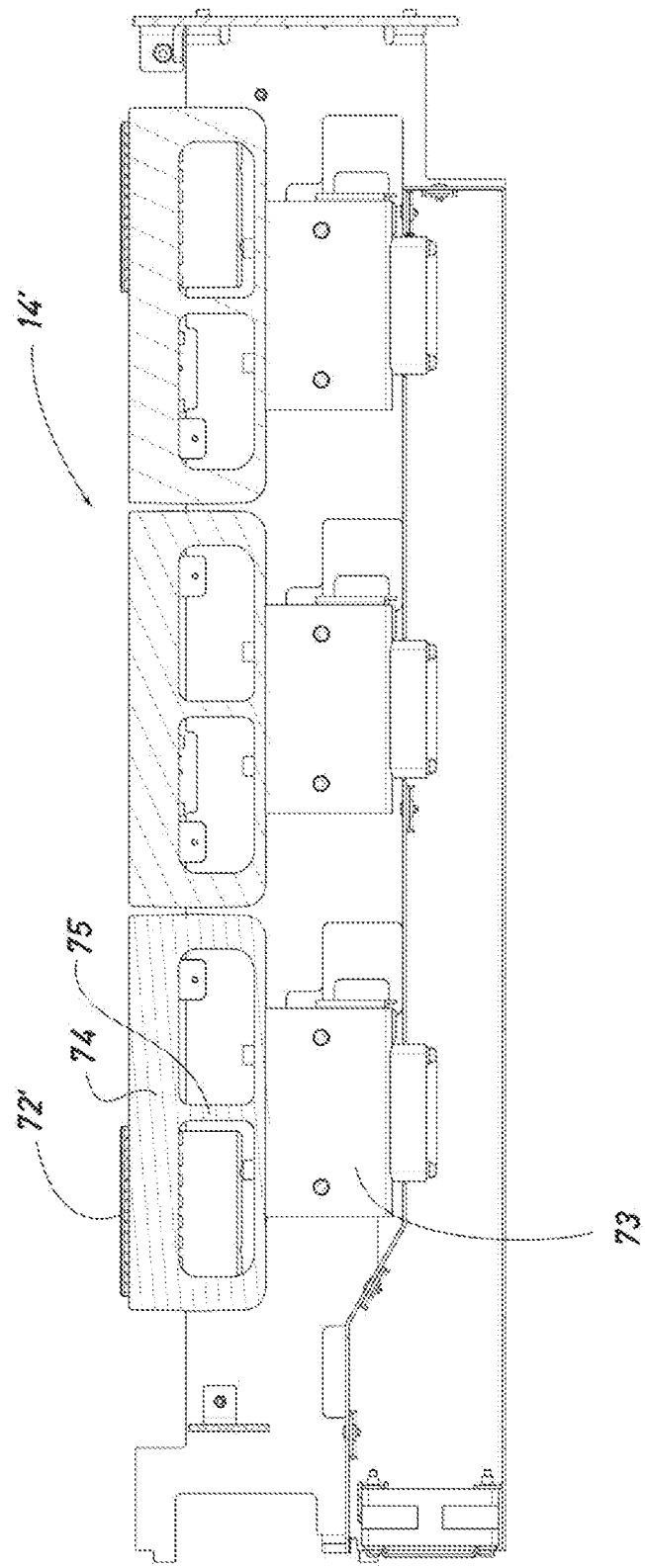
FIG. 18 shows a side view with partial cross-section of the gel card incubator device.

FIGS. 18 and 18 bis show an incubator device —14'— that has multiple supports —72— for the gel cards —72'— and Peltier units —73— for the heating/cooling of the same, said supports —72— being incorporated into aluminium frames —74—with a structure similar to a U shape and a central arm —75—that allows easy heat transfer.

Figure 19:
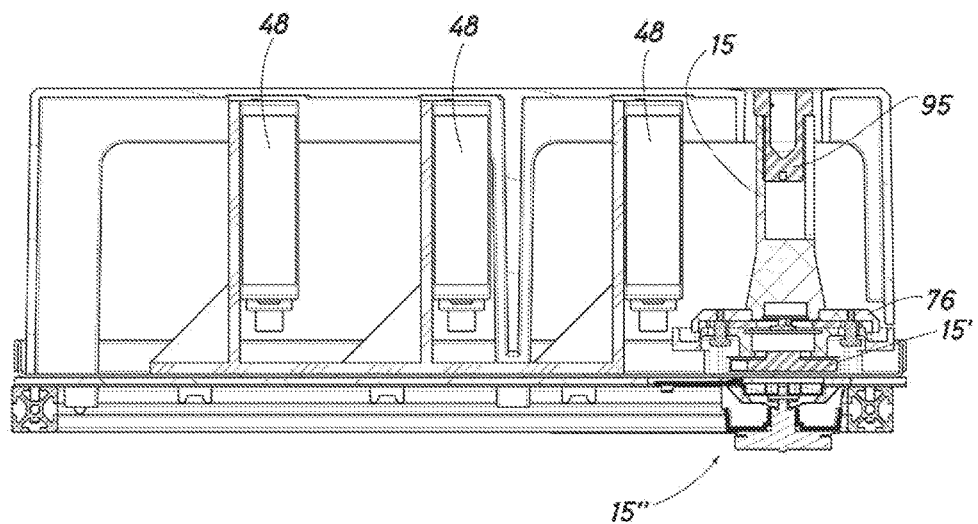
FIG. 19 shows a transverse cross-section view, showing the sample support, the dilution well and the intrusion detectors.

FIG. 19 shows the dilution well indicated previously with the number —15—. The well allows blood samples to be diluted without the use of disposable elements, since it is provided with an automatic post-dilution washing system which comprises a bowl —95— provided with a liquid inlet and outlet (not illustrated). The well has an orbital agitation system comprising an upper magnetic disc —15'— actuated by a magnetic-clutch motor —15"—, all located beneath the platform —76— that holds the well. Said rotating disc is provided with a position and rotation sensor.

Figure 20:
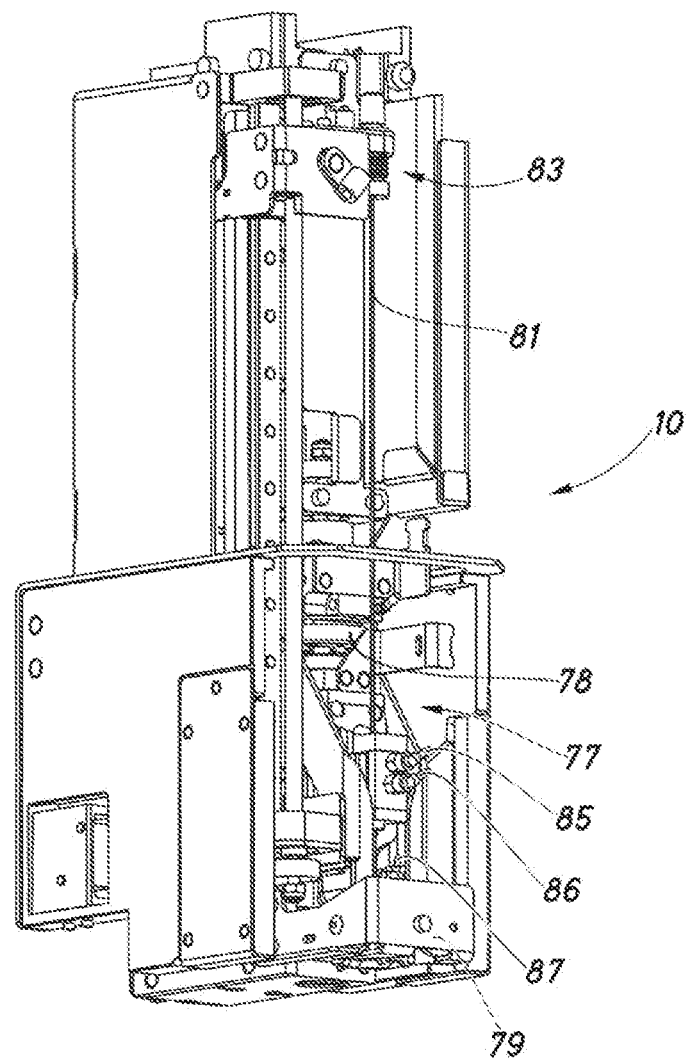
FIG. 20 shows a view from the right side of the perforating head.
Figure 21:
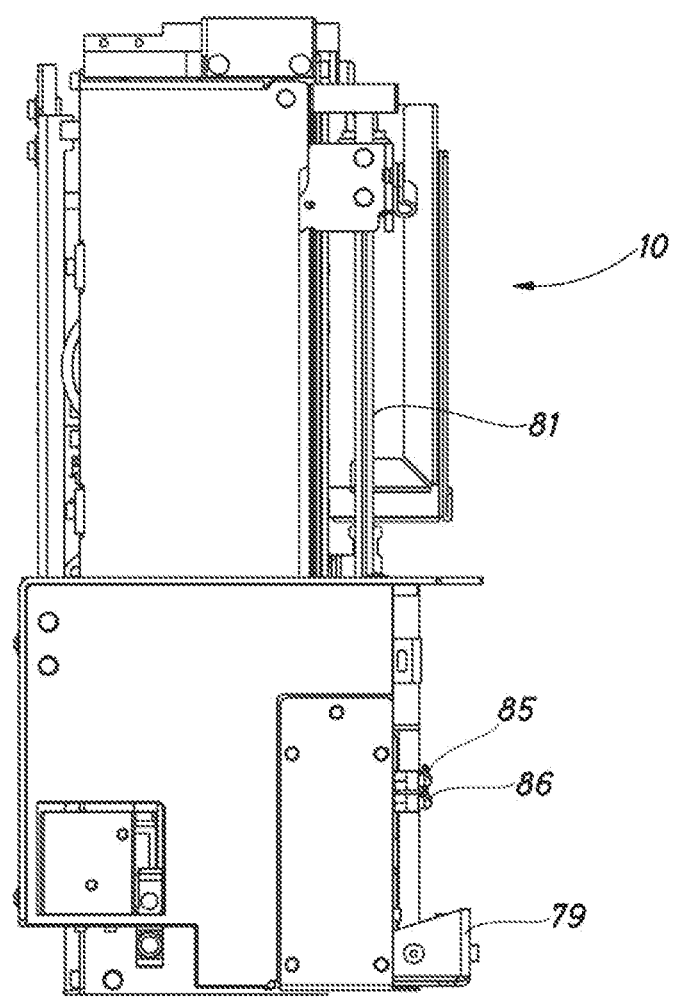
FIG. 21 shows an elevation view of the left side of the perforating head.
Figure 22:
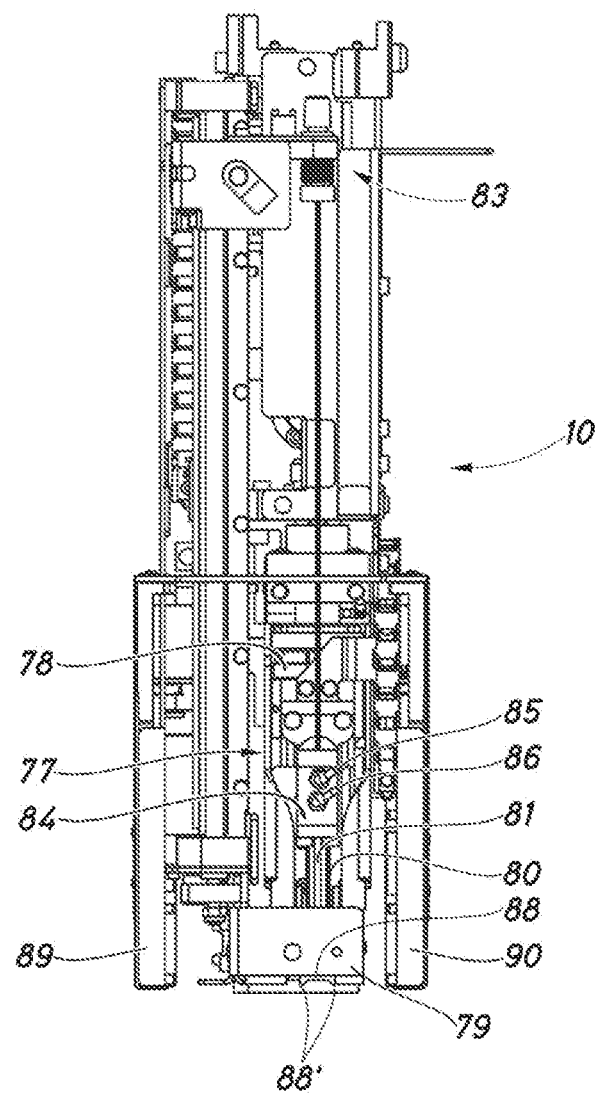
FIG. 22 shows a front view of the perforating head.

FIGS. 20 to 22 show a perforating and pipetting head in a perspective view, a front elevation view and a side elevation view. Said head —10— is intended to be suspended and guided by its upper part on a supporting frame of the apparatus by means of the carriage —12— represented in FIGS. 1 and 2, which allows it to move in a transverse direction, and a longitudinal guide, which will be explained later. This allows optimisation of the space in the upper floor of the apparatus in which said head must work, so that said head can access the entire surface of its respective floor, without any dead or excluded zones.

The head has a movable assembly —77— which moves on a vertical spindle with its own actuating motor, said movable assembly —77— being provided with an intermediate magnetic clutch —78—, which allows the disconnection of the lower part of the movable assembly carrying the hold-down plate unit —88—, and which has guide means for two concentric probes, namely one probe —80— intended for perforating the rubber stoppers of sample tubes and a second concentric probe —81— intended for pipetting. Firstly, the probe —80— that perforates the rubber stopper of a sample tube is actuated, while said probe is pressed vertically by the hold-down plate unit —88— of said movable assembly —77—, and then the pipetting probe —81— is allowed to move, being moved by its upper end by its own means, generically indicated with the number —83—. This allows the perforating head, which is located on the tube holding the stopper, to work, pressing on the tube by means of the hold-down plate unit —88— and then causing the penetration of the outer probe —80—, which passes through the stopper and facilitates the subsequent passage of the probe —81— for pipetting of the liquid, which is carried out in accordance with the instructions of the electronic controller of the apparatus after determining the level of liquid in the interior of the sample tube and calculating the volume that must be used in the analysis cycle, which will determine the size of the volume to be pipetted. The head incorporates a system for the identification of samples and reagents.

After each working cycle, both the perforating probe and the pipetting probe must be washed. To this end, a washing liquid is used, which is collected immediately after washing, without any discontinuity over time. This makes it unnecessary to have any storage space for the washing liquid, since the delivery of washing liquid and the aspiration of the same, immediately after it touches the probe and said probe has been washed, are carried out simultaneously. In FIGS. 20 to 22 can be seen the washing unit 84 of the pipetting needle, showing the couplings —85— and —86— for the inlet and outlet of the washing liquid. In the hold-down plate unit —88— is incorporated the washing device of the perforating probe, which also receives washing liquid that is recovered immediately in a continuous circuit. One of the liquid couplings can be seen in FIG. 20, where it is indicated with the number —87—.

The hold-down plate unit —88— has a lower housing that essentially mates in form with the stoppered head of the sample tube on which it must operate, and also has means for centring the gel card, since the head must also act on the gel cards in the pipetting operation, for which reason the hold-down plate unit —88— has two pairs of centring lugs —88'— (of which only one is visible in FIG. 22), which make it possible to hold the gel card in place during the operations of insertion and removal of the probe, preventing any movement of said card.

The pipetting probe —81— is associated with a capacitance level-detecting system and another system for detecting correct pipetting. The purpose of the level-detecting system, as mentioned previously, is to determine the level of the fluid in the sample tube, in order to have a reference for the volume that must be removed for the analysis cycle. The correct pipetting detector is designed to control the pipetting in terms of fluidic control, indicating any pipetting errors produced by soiling or other factors.

The perforating and pipetting head is also provided with a sample and reagent identification system with a laser proximity detector housed in the body —79—, which allows detection of the presence of sample tubes and vials/bottles of reagents/diluents in the drawers, being located in a fixed position in the base of the head. The head is also provided with a barcode reading system comprising a structure with vertically moving elements —89— and —90— in which are housed two barcode readers which, by means of mirrors, are capable of reading in opposite directions. The overall width of the structure allows it to be lowered with the head situated above a rack, in such a way that the beams of the barcode readers are directed at the tubes/vials/bottles.

It should be noted that the provision of two separate probes, one for perforating and the other for pipetting, is intended to ensure that no soiling occurs in the stopper and to prevent contamination of the serum with blood. The perforating probe has the ability to perforate the rubber stopper of the sample tube and also to regulate the pressure between the interior of the tube and the atmosphere.

The hold-down plate moves together with the perforating probe, supporting the tube while the probe is withdrawn and having, as indicated previously, means for washing the interior and exterior of the perforating probe.

The hold-down plate and the perforating probe are moved by the action of a magnetic clutch mechanism, indicated with the number —78— in FIGS. 20 and 22, which separates when the hold-down plate reaches the stoppered tube.

Figure 23:
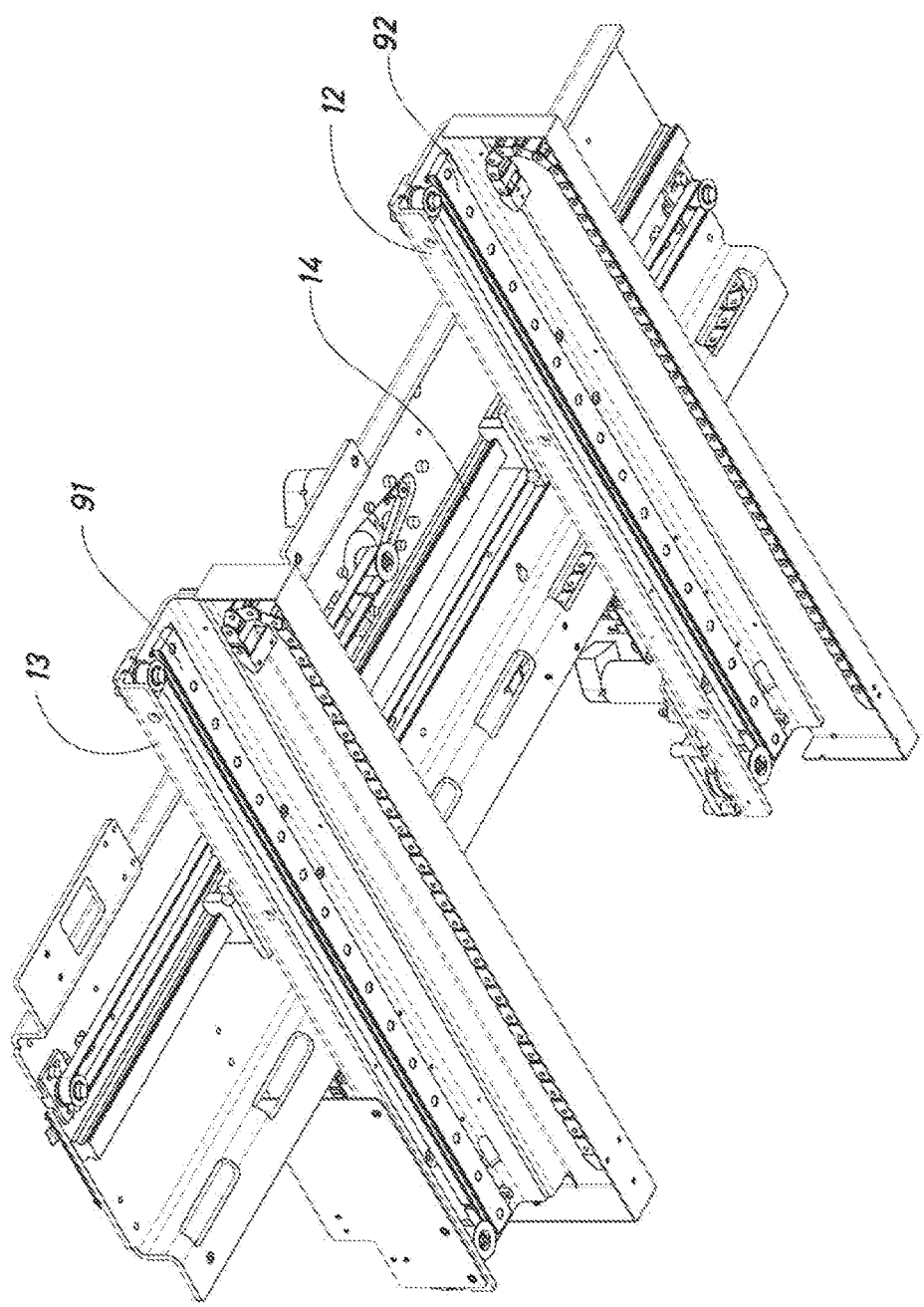
FIG. 23 shows a perspective view of the guides of the heads of the apparatus, from below.
Figure 24:
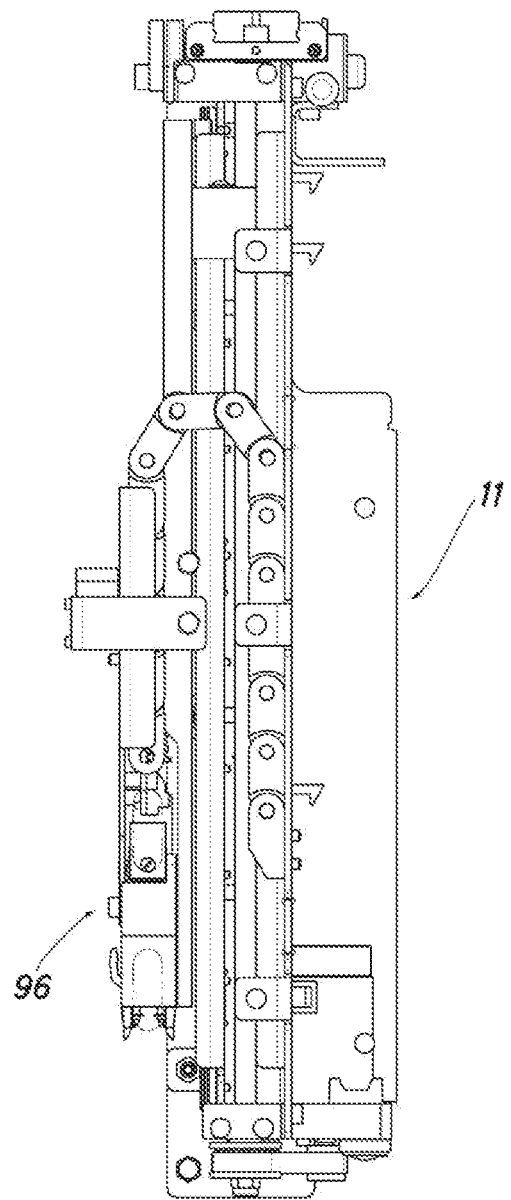
FIG. 24 shows a side view of the card-handling head.

FIG. 23 shows the upper guides of the apparatus which allow the movements of the heads along the X and Y axes. The perforation and pipetting and card transport heads, not shown in this view, move along the respective carriages —12—and —13—, which have the respective transverse guides —91— and —92— along which the respective heads can move, driven by the corresponding motors and toothed belts or similar.

The carriages —12— and —13— are movable along the longitudinal guide 14—, also shown in FIG. 2, which allows the movements of the heads along the other coordinate axis, allowing them to reach any point in the assigned zone.

Figure 25:
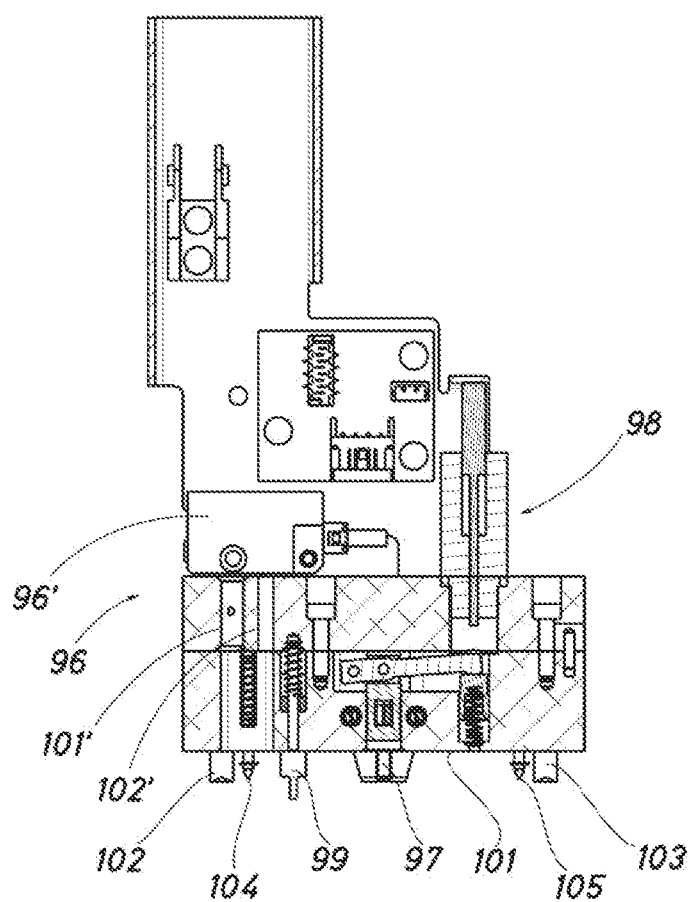
FIG. 25 shows a front view with cross-section.
Figure 26:
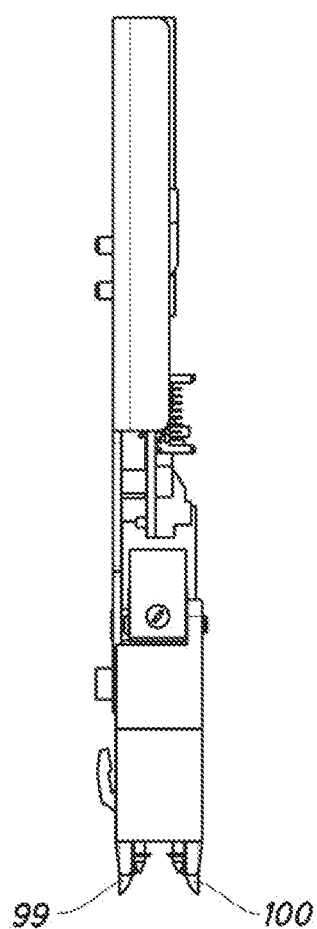
FIG. 26 shows a side view of the centring and clamping unit.

The card-handling head —11— has a vertically movable unit —96— which is provided with elements for centring and clamping a gel card. Said unit —96— has two clamps opposite each other, of which only one clamp —97— is shown in FIG. 25. Said clamps are suitable for holding a gel card by its upper edges and are actuated by a magnetic device —98—incorporated in said unit —96—. A further pair of retractable arms —99— and —100— are suitable for centring the gel cards by their side edges, stabilising the same for the subsequent action of the holding clamps —97—. Said unit —96— has on its bottom surface —101— two pairs of end lugs, indicated with the numbers —102— and —103—, for centring the gel card, and also two pairs of retractable pointed pins —104— and —105— suitable for acting on the flat upper face of the gel card. Also shown in said FIG. 25 is a laser emitter/receiver —96'— which emits a beam through the channel —102'— and is intended to detect the surface of the cards in order to confirm that the clamp is holding a card, as well as serving the function of performing a mobile inventory of cards in the drawers, centrifuges and incubators. The beam returns to the emitter/receiver through the channel —101'—.

The means with which the apparatus is provided allow it to operate automatically, offering numerous functional and security controls, notably the sample and reagent identification means comprised by both the perforating and pipetting head and the card transport head. This makes it possible, at the start of the work, for the apparatus to recognise each of the tubes, vials, bottles or cards individually, so that the electronic controller knows with precision the elements available for the work and their exact position. This information is updated for each movement carried out in the course of an analysis cycle, so that according to the analysis cycle to be conducted for each individual sample, the apparatus has the means for performing all the operations of the cycle, i.e. the pipetting of samples, reagents and diluents, the performance of dilutions if applicable, the dispensing of cards, the incubation of said cards if applicable, centrifugation, reading of the cards and notification of the results to the operator via the touch screen or by other means. In the event that the result is not clear, the apparatus has means for warning the operator accordingly and returning the card for visual inspection. In the event that the analysis has been successfully completed, the card will be removed and deposited in the scrap receptacle. In the event that, on completion of an analysis cycle, some of the wells of the card have not been used, the apparatus automatically places the card in a waiting zone, from where it will be automatically retrieved when use can be made of any of the unused wells for the performance of another analysis cycle. This way of proceeding helps to save on materials, has influence on the ecological general performance of the apparatus and makes it possible to reduce handling operations performed from the outside of the apparatus to the inside of the same for loading racks of cards, which in some machines were discarded after an analysis cycle regardless of the possibility of their partial recovery.

To summarise, for the purposes of greater clarity, the apparatus comprises:

According to one aspect, a containing body with a flat upper functional floor for containing receptacles of reagents, diluents and samples, as well as housings for gel cards and incubators for the same; a lower floor containing receptacles for washing liquids and the collection of waste and cards and for housing the fluidic control and electronic control system; a series of longitudinal and transverse guides associated with the upper part of the apparatus, suitable for carrying in suspension the moving heads of the apparatus, said heads being movable on the transverse guides; two heads, respectively for perforation and pipetting and for the transport of gel cards; two centrifuges and a gel card reader; and a folding touch screen providing information and control.

According to another aspect, the base of the upper floor of the apparatus is made impermeable to liquids and has a flat overall structure in order to prevent liquids from reaching any electrical and electronic parts and to facilitate washing. The upper floor also has a zone intended to contain the supports for receptacles of samples, diluents and reagents, and another zone intended to contain the gel cards, said zones being separated by an intermediate zone occupied by the card incubators.

For linear guidance and braking on completion of the insertion of the supports for reagent, diluent and sample receptacles, the base of the upper floor is provided, in the zones that are to be occupied by the respective supports, with flat magnetic strips which combine with flat magnetic strips of mating polarity located in the base of the movable supports for said reagent, diluent and sample receptacles, providing linear magnetic guidance during the insertion and extraction of each of said supports and braking of the same on completion of their insertion, avoiding the need for mechanical guides for said supports.

The supports for the reagent, diluent and sample receptacles comprise:
  a zone intended to receive a support for vials of reagents, provided with means for their agitation,
  a zone intended to receive a support for reagent receptacles that do not have to be agitated, and
  another zone intended to receive receptacles for diluent liquids;
and each support for reagent and diluent receptacles is provided in its lower base with magnetic strips of a polarity suitable for mating with those of the floor of the apparatus in order to allow magnetic guidance and braking of said support; additionally, each support for reagent and diluent receptacles has a magnetic fastening device which is automatically activated in the position of maximum insertion of the support and requires instructions from the touch screen for its deactivation, allowing it to be opened.

According to another aspect, the reagent receptacles are slightly inclined relative to the vertical. To achieve this, the bottoms of the housings for the reagent receptacles are slightly inclined, in order to impart an inclination to the receptacles.

According to another aspect, the upper floor is provided with a system of infra-red emitters in a bottom wall and sensors in a wall adjoining the front of the apparatus in order to detect any uncontrolled intrusions, triggering an alarm signal in the event of any such intrusion.

According to another aspect, the gel card centrifuge devices are coupled in suspension from the base of the upper floor of the apparatus beneath the card drawers, having an opening for each of said centrifuge devices that is accessible to the card-handling head through corresponding openings in the base of the upper floor of the apparatus.

The incubators arranged between the reagent, diluent and sample zone and the card zone have multiple modules with slots for receiving cards and heating/cooling elements using Peltier cells, said modules being integrated by means of aluminium elements in contact with the Peltier cells and carriers of the card-receiving slots.

Each of the supports for racks of sample tubes comprises a base containing two housings, each of these being intended to receive an individual rack for multiple sample tubes, said support having on its lower face longitudinal magnetic strips mating with the magnetic strips of the base of the upper floor for longitudinal guidance and braking of said support on completion of the insertion, said support also having a magnetic fastening which is automatically activated after the insertion of the support and can be deactivated via the touch screen.

The system of guides for guiding the movements of the heads along two coordinate axes consists of a longitudinal guide attached to the top part of the apparatus, on which can move, driven by individual actuation means, respective carriages for the perforating and pipetting head and the card transport head, which are movable by their own actuation means on respective guides of said carriages, which are arranged transversely, so that together the heads can perform a bi-directional movement covering all the zones of the plane assigned to each of them.

The head for perforating and pipetting reagent, diluent and sample tubes has an outer tubular probe provided with its own drive means, intended for perforating the rubber stoppers of the sample tubes, which contains within itself a pipetting probe that is actuated axially in an independent manner, making it possible to perform separately the perforation of the rubber stopper and the subsequent movement of the pipetting probe in order to detect the level of liquid in the receptacle and then to pipette said liquid.

The pipetting probe is associated with means for detecting the level of liquid in the receptacle and with means for controlling the pipetting, said level-detecting means being a capacitance level-detecting device.

According to another aspect, the movable assembly of the perforating and pipetting head is provided with a magnetic clutch which allows the separation of the assembly when the hold-down plate reaches the sample tube.

The perforating head has a hold-down plate unit suitable for pressing on the stopper of a sample tube during the operation of perforation and pipetting, and said hold-down plate unit also has projections shaped to mate with the upper edge of a gel card in order to immobilise said card when the pipetting is performed on it.

Both the perforating and pipetting head and the card transport head have means for identifying individual vials of reagents, diluents and samples and cards, said receptacle identification means allowing a first step of identifying all the available receptacles in the upper floor of the apparatus, this information being incorporated into the central electronic controller for the purposes of performing a mobile inventory of each of the positions.

The touch screen is arranged on a support with an articulated arm on one side of the apparatus, and can be unfolded for operational availability or folded up against the side of the apparatus, thus reducing the space occupied.

According to another aspect, the card transport head has a vertically movable unit carrying means for clamping and centring the card before and during its transport, comprising a laser detection system for detecting the presence of a card while it is transported by the clamp, as well as detecting the cards in the card drawers, incubators and centrifuges, situating the clamp at the corresponding height, two magnetically actuated clamps suitable for holding the gel card by the edges of its upper base and also having retractable means for prior centring, means for securing the gel card and fixed posts for centring the same, in such a way that the prior centring posts are retractable by means of a return spring and are suitable for adapting to the opposite sides of the upper base of the gel card prior to the actuation of the magnetic actuation posts for holding the card and the card securing means associated with the lower face of the movable unit of the head consist of pairs of retractable pointed pins suitable for acting on the upper face of the gel card being handled. In addition, the lower face has respective pairs of fixed posts near the ends of the movable unit for centring the gel card by the ends of its upper base.

Although the apparatus for immunohaematological analysis that forms the subject of the present invention has been described and illustrated based on a representative embodiment, it must be understood that said embodiment is in no way limitative of the present invention, and therefore any variations covered directly or by way of equivalence in the content of the attached claims must be considered to be included in the scope of the present invention.

What is claimed is:

1. An apparatus for automatic immunohematological analysis on gel cards, wherein the apparatus comprises:
    a) a containing body with a flat functional upper floor containing receptacles of reagents, diluents and samples;
    b) a lower floor comprising receptacles for washing liquids and for collection of waste liquid and scrap cards, and for housing a fluidic and electronic control system;
    c) a first transverse guide and a second transverse guide associated with an upper part of the apparatus, the first transverse guide being configured to attach to a first moving head of the apparatus, and the second transverse guide being configured to attach to a second moving head of the apparatus, such that the first and second moving heads are configured to be movable on the first and second transverse guides in a transverse direction, the first moving head comprising a first probe configured for perforating stoppers of receptacles and a second probe configured for pipetting a liquid in the receptacle, and the second moving head comprising a clamp configured for transporting the gel cards;
    d) a longitudinal guide associated with the upper part of the apparatus configured to attach to the first and second transverse guides, such that the first and second transverse guides are configured to be movable on the longitudinal guide in a longitudinal direction;
    e) two gel card centrifuges and a gel card reader;
    f) a folding information and control touch screen;
    g) wherein the flat functional upper floor is comprised of a single working level, the single working level having the receptacles on its top side, said receptacles containing reagents, diluents, and samples as the liquid in the receptacles, said single working level further comprising a dilution well, and card drawers housing the gel cards, each card drawer being screwed to a metal sheet base and supported by two linear guides and configured to be opened and closed, the single working level having on its bottom side, underneath the top side, the two centrifuges, and the gel card reader, and the upper floor having an opening to send gel cards to a scrap receptacle in the lower floor for receiving scrap cards to be scrapped or temporarily stored for their eventual re-use; and
    h) wherein gel card incubators are arranged along a central area on the top side of the single working level of the flat functional upper floor between a zone of the apparatus for reagents, diluents, samples and the dilution well, and a zone of the apparatus for card drawers, the centrifuges, the gel card reader, and the opening to the scrap receptacle for scrap cards.

2. The apparatus according to claim 1, wherein a base of the flat functional upper floor of the apparatus is made impermeable to liquids and has a flat overall structure in order to prevent liquids from reaching any electrical and electronic parts and to facilitate washing.

3. The apparatus according to claim 1, wherein the flat functional upper floor has a zone containing movable supports for receptacles for reagents, diluents and samples, and a zone containing the gel cards.

4. The apparatus according to claim 1, wherein a base of the flat functional upper floor is comprised of flat magnetic strips which combine with flat magnetic strips of mating polarity located in a base of movable supports for receptacles for reagents, diluents and samples, wherein the base of the flat functional upper floor is configured for providing linear magnetic guidance during an insertion and an extraction of the supports and braking of the supports on completion of the insertion.

5. The apparatus according to claim 4, wherein the movable supports for receptacles for reagents, diluents and samples have:
    a zone to receive receptacles to be agitated,
    a zone to receive receptacles that do not have to be agitated.

6. The apparatus according to claim 5, wherein the receptacles for reagents, diluents and samples are inclined relative to a vertical axis.

7. The apparatus according to claim 6, wherein the lower floor of the apparatus is inclined.

8. The apparatus according to claim 4, wherein the movable supports for the receptacles for reagents, diluents and samples are automatically closed magnetically in a position of maximum insertion of the supports and require instructions from the touch screen to be opened.

9. The apparatus according to claim 1, wherein the flat functional upper floor comprises a system of infra-red emitters in a bottom wall and sensors in a wall adjoining the front of the apparatus in order to detect any uncontrolled intrusions, triggering an alarm signal in the event of any such intrusion.

10. The apparatus according to claim 1, wherein the gel card centrifuges are coupled in suspension from a base of the flat functional upper floor of the apparatus beneath the card drawers, the base of the flat functional upper floor of the apparatus beneath the card drawers having an opening for each of the centrifuges that is accessible to the second head for transporting the gel cards through the openings in the base of the flat functional upper floor of the apparatus.

11. The apparatus according to claim 1, wherein the gel card incubators have multiple modules each module having a plurality of slots for receiving the gel cards, the slots being supported by aluminum elements of the modules, the aluminum elements being in contact with heating/cooling elements of Peltier cells.

12. The apparatus according to claim 1, wherein supports for racks of sample receptacles comprises a base containing two housings, each housing being intended to receive an individual rack for multiple sample receptacles, the supports having on their lower face longitudinal magnetic strips mating with magnetic strips of the base of the flat functional upper floor for longitudinal guidance and braking of the supports on completion of the insertion, the supports also having a fastening element which is automatically activated after the insertion of the supports and can be deactivated via the touch screen.

13. The apparatus according to claim 1, wherein the guides for guiding the movements of the first and second moving heads comprises a bi-directional guide, on which can move respective carriages for the first and second moving heads, which are movable such that together the first and second moving heads can perform longitudinal and transverse movements covering the entire flat functional upper floor.

14. The apparatus according to claim 1, wherein the first probe of the first head is an outer tubular probe comprising its own driver, the first probe containing within itself the second probe that is actuated axially in an independent manner, making it possible to perform separately the perforation of stoppers of receptacles and a subsequent movement of the second probe in order to determine a level of a liquid in a receptacle and to pipette the liquid.

15. The apparatus according to claim 14, wherein the second probe is associated with a detector for detecting the level of liquid in the receptacle and with a controller for controlling the pipetting.

16. The apparatus according to claim 15, wherein the detector for detecting the level of liquid comprises a capacitance level-detecting device.

17. The apparatus according to claim 1, further comprising a hold-down plate, wherein a movable assembly of the first head comprises a magnetic clutch which is configured for separation of the movable assembly when the hold-down plate reaches a sample receptacle.

18. The apparatus according to claim 14, wherein the first head has a hold-down plate configured to press on the stopper of a sample receptacle and hold the sample receptacle in place during the operation of perforation and pipetting.

19. The apparatus according to claim 17, wherein the hold-down plate comprises projections shaped to mate with the upper edge of a gel card in order to immobilize the card when pipetting is performed by the first head on the card.

20. The apparatus according to claim 1, wherein both the first moving head and the second moving head have receptacle identifiers for identifying the receptacles of reagents, and samples.

21. The apparatus according to claim 20, wherein the receptacle identifiers allow for an identification of the receptacles in the flat functional upper floor of the apparatus, wherein the identification information is incorporated into the fluidic and electronic control system for generating a mobile inventory of the receptacles.

22. The apparatus according to claim 1, wherein the touch screen is arranged on a support with an articulated arm on one side of the apparatus, and can be unfolded for operational availability or folded up against the side of the apparatus, thus reducing the space occupied.

23. The apparatus according to claim 1, wherein the second moving head has a vertically movable unit carrier for clamping and centering the card before and during its transport, the second head comprising a laser detection system for detecting the presence of a card while it is transported by the clamp, as well as detecting the gel cards in card drawers, gel card incubators and gel card centrifuges, and situating the clamp at the corresponding height, and further comprising two magnetically actuated clamps suitable for holding the gel card by the edges of its upper base and also having a retractor for prior centering, pairs of retractable pointed pins for securing the gel card and pairs of fixed lugs for centering the same.

24. The apparatus according to claim 23, wherein the pairs of retractable pointed pins are retractable by a return spring and are suitable for adapting to the opposite sides of the upper base of the gel card prior to an actuation of magnetic actuation posts for holding the card.

25. The apparatus according to claim 23, wherein the card is secured to a lower face of the second moving head by the pairs of retractable pointed pins configured to contact the upper face of the gel card being handled.

26. The apparatus according to claim 23, further comprising a plurality of pairs of fixed lugs near the ends of the movable unit for centering the gel card.

27. The apparatus according to claim 1, wherein a rack of gel cards is held in a working position by end lugs of the rack of cards, which are retained, respectively, at one end by a flexible claw of one of the card drawers and at the other end by a fixed lug of a fixed structure of the flat functional upper floor.

* * * * *